(12) United States Patent
Nagashima et al.

(10) Patent No.: US 10,000,515 B2
(45) Date of Patent: Jun. 19, 2018

(54) HYDROSILYLATION REACTION CATALYST

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Fukuoka (JP); Yusuke Sunada, Fukuoka (JP); Atsushi Tahara, Fukuoka (JP); Daisuke Noda, Fukuoka (JP); Hiroe Soejima, Fukuoka (JP); Koji Sakuta, Annaka (JP)

(73) Assignees: KYUSHU UNIVERSITY, NATIONAL UNIVERSITY CORPORATION, Fukuoka-Shi (JP); SHIN-ETSU CHEMICAL CO., LTD., Tokyo (JP)

(*) Notice: Subject to any disclaimer, the term of this patent is extended or adjusted under 35 U.S.C. 154(b) by 0 days. days.

(21) Appl. No.: 15/503,266

(22) PCT Filed: Aug. 12, 2015

(86) PCT No.: PCT/JP2015/072839
§ 371 (c)(1),
(2) Date: Feb. 10, 2017

(87) PCT Pub. No.: WO2016/024611
PCT Pub. Date: Feb. 18, 2016

(65) Prior Publication Data
US 2017/0260215 A1  Sep. 14, 2017

(30) Foreign Application Priority Data
Aug. 12, 2014 (JP) ................. 2014-164194

(51) Int. Cl.
C07F 7/04 (2006.01)
C07F 7/08 (2006.01)
B01J 31/22 (2006.01)

(52) U.S. Cl.
CPC ......... *C07F 7/0829* (2013.01); *B01J 31/2273* (2013.01); *B01J 2231/323* (2013.01); *B01J 2531/821* (2013.01); *B01J 2531/822* (2013.01); *B01J 2531/842* (2013.01); *B01J 2531/845* (2013.01); *B01J 2531/847* (2013.01)

(58) Field of Classification Search
CPC ................ C07F 7/0829; B01J 31/2273; B01J 2231/323; B01J 2531/82; B01J 2531/84
USPC ....................................... 556/456
See application file for complete search history.

(56) References Cited

U.S. PATENT DOCUMENTS

| | | |
|---|---|---|
| 4,992,573 A | 2/1991 | Lewis |
| 5,389,404 A | 2/1995 | Armstrong |
| 5,523,436 A | 6/1996 | Dauth et al. |
| 5,561,231 A | 10/1996 | Dauth et al. |
| 6,124,418 A | 9/2000 | Crivello et al. |
| 6,303,728 B1 | 10/2001 | Hagimori et al. |
| 6,492,525 B1 | 12/2002 | Bertrand et al. |
| 6,737,531 B1 | 5/2004 | Dioumaev et al. |
| 6,803,440 B2 | 10/2004 | Marko et al. |
| 7,019,145 B2 | 3/2006 | Buisine et al. |
| 7,563,741 B2 | 7/2009 | Brummer et al. |
| 7,803,893 B2 | 9/2010 | Hofmann et al. |
| 8,124,711 B2 | 2/2012 | Hofmann et al. |
| 8,236,915 B2 | 8/2012 | Delis et al. |
| 8,415,443 B2 | 4/2013 | Delis et al. |
| 8,895,770 B2 | 11/2014 | Lewis et al. |
| 9,073,950 B2 | 7/2015 | Kownacka et al. |
| 9,480,977 B2 | 11/2016 | Brandstadt et al. |
| 2003/0083454 A1 | 5/2003 | Marko et al. |
| 2004/0236054 A1 | 11/2004 | George et al. |
| 2011/0160454 A1 | 6/2011 | Yoo et al. |
| 2014/0249311 A1 | 9/2014 | Brandstadt et al. |

FOREIGN PATENT DOCUMENTS

| | | |
|---|---|---|
| CN | 102351907 A | 2/2012 |
| CN | 102516314 A | 6/2012 |
| EP | 2 114 977 A1 | 11/2009 |
| FR | 2 911 876 A1 | 8/2008 |
| JP | 1-315344 A | 12/1989 |
| JP | 6-136126 A | 5/1994 |

(Continued)

OTHER PUBLICATIONS

Mo, Zhenbo et al., "Anchoring of Silyl Donors on a N-Heterocyclic Carbene through the Cobalt-Mediated Silylation of Benzylic C—H Bonds", Angewandte Chemie. International Edition, 2013, vol. 52, pp. 10845-10849.*
Adams et al., "The Catalytic Activity of Transition Metal Complexes of Sterically Hindered Isocyanides", Journal of Molecular Catalysis, 1985, vol. 29, pp. 201-208.
Bart et al., "Preparation and Molecular and Electronic Structures of Iron(0) Dinitrogen and Silane Complexes and Their Application to Catalytic Hydrogenation and Hydrosilation", J. Am. Chem. Soc., 2004, vol. 126, pp. 13794-13807.
Brookhart et al., "Mechanism of a Cobalt(III)-Catalyzed Olefin Hydrosilation Reaction: Direct Evidence for a Silyl Migration Pathway", J. Am. Chem. Soc., 1993, vol. 115, pp. 2151-2156.
Chalk et al., "Dicobalt Octacarbonyl as a Catalyst for Hydrosilation of Olefins", J . Am. Chem. Soc., 1965, vol. 87, No. 16, pp. 1133.
Chalk et al., "Homogeneous Catalysis. IV. Some Reactions of Silicon Hydrides in the Presence of Cobalt Carbonyls", Journal of the American Chemical Society, Mar. 29, 1967, vol. 89, No. 7, pp. 1640-1647.

(Continued)

*Primary Examiner* — Sudhakar Katakam
*Assistant Examiner* — Kofi Adzamli
(74) *Attorney, Agent, or Firm* — Birch, Stewart, Kolasch & Birch, LLP

(57) ABSTRACT

A hydrosilylation reaction catalyst prepared from: a catalyst precursor comprising a transition metal compound, excluding platinum, belonging to group 8-10 of the periodic table, e.g., iron acetate, cobalt acetate, nickel acetate, etc.; and a ligand comprising a carbine compound such as 1,3-dimesitylimidazol-2-ylidene, etc.. The hydrosilylation reaction catalyst has excellent handling and storage properties. As a result of using this catalyst, a hydrosilylation reaction can be promoted under gentle conditions.

7 Claims, 3 Drawing Sheets

(56) References Cited

FOREIGN PATENT DOCUMENTS

| | | |
|---|---|---|
| JP | 6-263780 A | 9/1994 |
| JP | 7-149780 A | 6/1995 |
| JP | 2001-131231 A | 5/2001 |
| JP | 3174616 B2 | 6/2001 |
| JP | 2003-516230 A | 5/2003 |
| JP | 3599669 B2 | 12/2004 |
| JP | 3854151 B2 | 12/2006 |
| JP | 4007467 B2 | 11/2007 |
| JP | 4249702 B2 | 4/2009 |
| JP | 4934190 B2 | 5/2012 |
| JP | 5032561 B2 | 9/2012 |
| JP | 2012-532884 A | 12/2012 |
| JP | 2012-532885 A | 12/2012 |
| JP | 2013-544824 A | 12/2013 |
| JP | 2014-502271 A | 1/2014 |
| JP | 2014-503507 A | 2/2014 |
| WO | WO 2008/095785 A1 | 8/2008 |
| WO | WO 2010/016416 A1 | 2/2010 |
| WO | WO 2013/043783 A2 | 3/2013 |
| WO | WO 2013/043785 A2 | 3/2013 |
| WO | WO 2013/043787 A2 | 3/2013 |
| WO | WO 2013/043846 A1 | 3/2013 |
| WO | WO 2013/043912 A2 | 3/2013 |
| WO | WO 2013/081794 A1 | 6/2013 |
| WO | WO 2014/021908 A1 | 2/2014 |

OTHER PUBLICATIONS

Chalk, "The Hydrosilation of Olefins Catalyzed by Some Rhodium and Cobalt Complexes", Journal of Organometallic Chemistry, 1970, vol. 21, pp. 207-213.

Chatani et al., "The $Co_2(C0)_8$-Catalyzed Hydrosilylation of Oxygen-Containing Olefins: Silylmetalation as a Key Step", Chemistry Letters, 2000, pp. 14-15.

Cornish et al., "Homogeneous Catalysis VI .Hydrosilylation Using Tris(Pentanedionato)Rhodium(III) or Tetrakis(μ-Acetato)Dirhodium(II) as Catalyst", Journal of Organometallic Chemistry, 1979, vol. 172, pp. 153-163.

Hill et al., "Rhodium Carbene Complexes as Hydrosilylation Catalysts", Journal of Organometallic Chemistry, 1977, vol. 137, pp. 293-300.

Hyder et al., "Oligomerization and regioselective hydrosilylation of styrenes catalyzed by cationic allyl nickel complexes bearing allylphosphine ligands", Dalton Trans., 2007, pp. 3000-3009.

Imlinger et al., "Rh(1,3-bis(2,4,6-trimethylphenyl)-3,4,5,6-tetrahydropyrimidin-2-ylidene)(COD) tetrafluoroborate, an unsymmetrical Rh-homoazallylcarbene: synthesis, X-ray structure and reactivity in carbonyl arylation and hydrosilylation reactions", Journal of Organometallic Chemistry, 2005, vol. 690, pp. 4433-4440.

International Search Report for PCT/JP2015/072839 dated Nov. 10, 2015.

Junquera et al., "R-Allyl Nickel(II) Complexes with Chelating N-Heterocyclic Carbenes: Synthesis, Structural Characterization, and Catalytic Activity", Organometallics, 2012, vol. 31, pp. 2175-2183, total 12 pages.

Kakiuchi et al., "Completely selective synthesis of ( E)-β-( triethylsilyl)styrenes by $Fe_3(CO)_{12}$-catalyzed reaction of styrenes with triethylsilane", Journal of Organometallic Chemistry, 1993, vol. 456, pp. 45-47.

Kamata et al., "Catalytic Hydrosilylation of Alkenes by Iron Complexes Containing Terpyridine Derivatives as Ancillary Ligands", Organometallics, 2012, vol. 31, pp. 3825-3828.

Kiso et al., "Silicon Hydrides and Nickel Complexes I. Phosphine-Nickel(II) Complexes as Hydrosilylation Catalysts", Journal of Organometallic Chemistry, 1973, vol. 50, pp. 297-310.

Li et al., "Synthesis of rhodium N-heterocyclic carbene complexes and their catalytic activity in the hydrosilylation of alkenes in ionic liquid medium", Journal of Organometallic Chemistry, 2011, vol. 696, pp. 2116-2121.

Lipschutz et al., "Synthesis and reactivity of a conveniently prepared two-coordinate bis(amido) nickel(II) complex", Chem. Commun., 2012, vol. 48, pp. 7146-7148.

Maciejewski et al., "Catalysis of hydrosilylation Part XXXIV. High catalytic efficiency of the nickel equivalent of Karstedt catalyst [{Ni(η-$CH_2$=$CHSiMe_2$)$_2$O}$_2${μ-(η-$CH_2$=$CHSiMe_2$)$_2$O}]", Journal of Organometallic Chemistry, 2000, vol. 597, pp. 175-181.

Magomedov et al., "Hydrosilylation of Olefins in the Presence of Metal Carbonyls", Journal of Organometallic Chemistry, 1978, vol. 149, pp. 29-36.

Mo et al., "Anchoring of Silyl Donors on a N-Heterocyclic Carbene through the Cobalt-Mediated Silylation of Benzylic C—H Bonds", Angewandte Chemie. International Edition, 2013, vol. 52, pp. 10845-10849, total 7 pages.

Naumov et al., "Selective Dehydrogenative Silylation-Hydrogenation Reaction of Divinyldisiloxane with Hydrosilane Catalyzed by an Iron Complex", Journal of the American Society, 2012, vol. 134, pp. 804-807.

Nesmeyanov et al., "Addition, Substitution, and Telomerization Reactions of Olefins in the Presence of Metal Carbonyls or Colloidal Iron", Tetrahedron, 1962, vol. 17, pp. 61-68.

Reichel et al., "Photochemistry of Cobalt Carbonyl Complexes Having a Cobalt-Silicon Bond and Its Importance in Activation of Catalysis", Inorg. Chem., 1980, vol. 19, pp. 3858-3860.

Schroeder et al., "Pentacarbonyliron(0) Photocatalyzed Reactions of Trialkylsilanes With Alkenes", Journal of Organometallic Chemistry, 1977, vol. 128, pp. 345-358.

Takeshita et al., "The Catalyzed Reaction of α,β-Unsaturated Esters with Various Hydrosilanes", J . Org. Chem., 1987, vol. 52, pp. 4864-4868.

Tondreau et al., "Iron Catalysts for Selective Anti-Markovnikov Alkene Hydrosilylation Using Tertiary Silanes", Science, 2012, vol. 335, pp. 567-570.

Tondreau et al., "Synthesis, Electronic Structure, and Alkene Hydrosilylation Activity of Terpyridine and Bis(imino)pyridine Iron Dialkyl Complexes", Organometallics, 2012, vol. 31, pp. 4886-4893.

Truscott et al., "Well-defined NHC-rhodium hydroxide complexes as alkene hydrosilylation and dehydrogenative silylation catalysts", Dalton Transactions, 2013, vol. 42, pp. 270-276.

Written Opinion of the International Searching Authority for PCT/JP2015/072839 (PCT/ISA/237) dated Nov. 10, 2015.

\* cited by examiner

HYDROSILYLATION REACTION CATALYST

TECHNICAL FIELD

This invention relates to a hydrosilylation catalyst and more particularly, to a hydrosilylation catalyst formed from a metal compound serving as a catalyst precursor and a carbene compound serving as a ligand component.

BACKGROUND ART

Hydrosilylation reaction which is addition reaction of a Si—H functional compound to a compound having a carbon-carbon double bond or triple bond is a useful means for the synthesis of organosilicon compounds and an industrially important synthesis reaction.

As the catalyst for hydrosilylation reaction, Pt, Pd and Rh compounds are known. Among others, Pt compounds as typified by Speier catalyst and Karstedt catalyst are most commonly used.

While several problems arise with reaction in the presence of Pt compounds as the catalyst, one problem is that upon addition of a Si—H functional compound to terminal olefin, a side reaction due to internal rearrangement of olefin takes place. Since this system does not exert addition reactivity to the internal olefin, unreacted olefin is left in the addition product. To drive the reaction to completion, it is necessary to use an excess amount of olefin in advance by taking into account the fraction left as a result of side reaction.

Another problem is that the selectivity of α- and β-adducts is low depending on the type of olefin.

The most serious problem is that all the center metals Pt, Pd and Rh are quite expensive noble metal elements. As metal compound catalysts which can be used at lower cost are desired, a number of research works have been made thereon.

For example, reaction in the presence of iron-carbonyl complexes ($Fe(CO)_5$, $Fe_3(CO)_{12}$) is known from Non-Patent Document 1, although this reaction requires reaction conditions including as high a temperature as 160° C. or light irradiation (Non-Patent Document 2).

For these iron-carbonyl complexes, it is reported in Non-Patent Document 3 and Patent Document 1 that dehydrogenation silylated products are obtained rather than the addition reaction.

Also Non-Patent Document 4 and Patent Document 2 report a reaction of methylvinyldisiloxane and methylhydrogendisiloxane in the presence of an iron-carbonyl complex coordinated with a cyclopentadienyl group. Since dehydrogenation silylation reaction takes place along with the relevant reaction, the selectivity of addition reaction is low.

With respect to reaction in the presence of an iron catalyst having a terpyridine ligand (Non-Patent Document 5), a large excess of a reducing agent ($NaBHEt_3$) is necessary as a reaction co-agent. Although $PhSiH_3$ and $Ph_2SiH_2$ add to olefins, more useful trialkylsilanes, alkoxysilanes and siloxanes have poor addition reactivity to olefins.

Non-Patent Document 6 reports that from reaction in the presence of an iron catalyst having a terpyridine ligand and a bistrimethylsilylmethyl group, an addition reaction product is obtained in high yields. This method needs some steps until the catalyst is synthesized, including first synthesizing a terpyridine-iron complex as a catalyst precursor and introducing a bistrimethylsilylmethyl group therein at a low temperature, which steps are not easy industrially.

Also, Non-Patent Documents 7 and 8 report iron complexes having a bisiminopyridine ligand. It is disclosed that they exhibit high reactivity to alkoxysilanes and siloxanes under mild conditions.

The reaction using the complex, however, suffers from several problems including low reactivity with internal olefin, the use of sodium amalgam consisting of water-prohibitive sodium and highly toxic mercury and requiring careful handling (or use of water-prohibitive $NaBEt_3H$) for complex synthesis, low stability of the complex compound itself, a need for a special equipment like a glove box for handling, and a need for storage in an inert gas nitrogen atmosphere at low temperature.

Non-Patent Documents 9 to 14 report examples of reaction in the presence of cobalt-carbonyl complexes (e.g., $Co_2(CO)_8$), but they are unsatisfactory in reaction yield and reaction molar ratio. No reference is made to addition reactivity to siloxanes.

Also an example of reaction of olefin with trialkylsilane in the presence of a cobalt-carbonyl complex substituted with a trialkylsilyl group is reported in Non-Patent Document 15, but the yield is low and the selectivity is low.

Non-Patent Document 16 reports reaction of olefin with trialkylsilane in the presence of a cobalt-phosphite complex coordinated with a cyclopentadienyl group, and Non-Patent Document 17 reports reaction of olefin with trihydrophenylsilane in the presence of a cobalt complex coordinated with N-heterocyclocarbene. Because of low stability, these complex compounds require a special equipment like a glove box for handling and an inert gas atmosphere and a low temperature for storage.

Also Patent Documents 3 to 6 report iron, cobalt and nickel catalysts having terpyridine, bisiminopyridine and bisiminoquinoline ligands. Like the above-cited Non-Patent Documents 6 to 8, there are problems including industrial difficulty of synthesis of a catalyst precursor or synthesis of the complex catalyst from the precursor, low stability of the complex compound itself, and a need for a special equipment for handling.

Patent Document 7 discloses a method of conducting reaction in the presence of a complex catalyst having a bisiminoquinoline ligand, using Mg(butadiene).2THF or $NaEt_3BH$ as the catalyst activator. There are the same problems as above and the yield of the desired product is less than satisfactory.

Many examples of the nickel complex catalyst are reported. For example, a catalyst having a phosphine ligand (Non-Patent Document 18) lacks in selectivity and requires careful handling and storage.

With a vinylsiloxane-coordinated catalyst (Non-Patent Document 19), a dehydrogenation silylated product becomes predominant, indicating low selectivity of addition reaction.

With an allylphosphine-coordinated catalyst (Non-Patent Document 20), the yield is low, and trihydrophenylsilane is not a substrate of industrial worth.

A bisamide-bearing catalyst (Non-Patent Document 21) needs careful handling and storage, and dihydrodiphenylsilane is not a substrate of industrial worth.

A catalyst having N-heterocyclocarbene ligand (Non-Patent Document 22) has low selectivity of reaction, and trihydrophenylsilane is not of industrial worth.

Many rhodium complex catalysts are reported. For example, catalysts having a carbonyl or cyclooctadienyl (COD) group and a N-heterocarbene ligand (Non-Patent Documents 23, 24) require handling and storage in an inert gas atmosphere because the complex compounds have low stability.

Non-Patent Document 25 discloses to conduct reaction in the presence of an ionic liquid in order to enhance reactivity. The step of separating the ionic liquid from the reaction product is necessary. Since the catalyst used therein has a COD group and a N-heterocarbene group as the ligand, the same problems as described above are left.

Also Non-Patent Document 26 reports an exemplary catalyst which allows for preferential progress of dehydrogenation silylation reaction.

Furthermore, Non-Patent Document 27 reports an example in which an isocyanide compound is added to a complex catalyst to form a catalyst, which is used in hydrosilylation reaction without isolation. A study on reactivity with three types of silanes shows that the order of reactivity is from dimethylphenylsilane, which gives the highest yield (yield 81%), next triethylsilane (yield 66%), to triethoxysilane (yield 40%). The reactivity with triethoxysilane which is of the most industrial worth among the three types of silanes is not so high, while the reactivity with siloxanes is reported nowhere.

In addition, the precursor catalyst having a COD group as the ligand requires careful handling and storage.

On the other hand, Non-Patent Document 28 reports that a rhodium catalyst having an acetylacetonato or acetate group enables addition reaction of triethoxysilane in high yields.

Although this method has the advantage of easy storage and handling of the catalyst, no study is made on reactivity with siloxanes which are more useful from the industrial standpoint.

In addition, rhodium is likewise an expensive noble metal element. Its catalytic function must be further increased to a higher activity before it can be used in practice as a platinum replacement.

The catalysts with their application to organopolysiloxanes being borne in mind include a catalyst having a phosphine ligand (Patent Document 8), a catalyst having an aryl-alkyl-triazenide group (Patent Document 9), a colloidal catalyst (Patent Document 10), a catalyst coordinated with a sulfide group (Patent Document 11), and a catalyst coordinated with an amino, phosphino or sulfide group and an organosiloxane group (Patent Document 12).

However, reactivity is empirically demonstrated with respect to only platinum, palladium, rhodium and iridium which are expensive metal elements. Thus the method is not regarded cost effective.

In Examples of Patent Documents 13 and 14, only well-known platinum catalysts are demonstrated to exert a catalytic effect while the structure which is combined with another metal to exert catalytic activity is indicated nowhere.

Patent Documents 15 to 17 disclose catalysts coordinated with carbene. Patent Document 15 does not discuss whether or not the catalyst is effective to hydrosilylation reaction.

Patent Documents 16 and 17 disclose catalysts coordinated with carbene and vinylsiloxane, but describe only platinum catalysts in Examples.

In addition, the metal catalysts coordinated with carbene require careful handling because the complex compounds have low storage stability.

Likewise, as an example of the catalyst coordinated with carbene, Patent Documents 27 and 28 disclose only platinum catalysts.

Also Patent Document 29 discloses a metal-carbene complex catalyst obtained from reaction of a Ni-carbene complex with a metal precursor. However, the Ni-carbene complex must be separately synthesized. The metal precursor to be reacted is a metal compound having a ligand such as phosphine or COD. The metal precursor having such a ligand is low in storage stability.

Patent Documents 30 and 31 disclose complex catalysts obtained by reacting Pd, Pt and Ni complexes having olefinic ligands with carbene. However, the metal complexes having olefinic ligands except well-known Pt catalysts having vinylsiloxane ligands are low in storage stability.

Patent Document 32 discloses a Co-carbene complex, which is active to hydrosilylation reaction on ketones.

Patent Documents 33 and 34 disclose the application of a metal-carbene complex to curing reaction of organopolysiloxane. Only Pt is referred to as the metal. The synthesis method is reaction of a well-known Pt complex having vinylsiloxane ligand with carbene.

Patent Documents 18 and 19 disclose ruthenium catalysts coordinated with $\eta^6$-arene or $\eta^6$-triene. These catalysts have inferior reactivity to platinum catalysts and require careful handling because the complex compounds have low storage stability.

Patent Documents 20 to 26 disclose a method of mixing a metal salt with a compound which coordinates to the metal and using the product as a catalyst rather than the use of metal complexes as the catalyst. Although these Patent Documents describe the progress of hydrosilylation with several exemplary combinations, the yield and other data are described nowhere, and the extent to which the reaction takes place is not evident.

For example, Patent Documents 21 and 22 describe Examples in which compounds corresponding to carbene are added to halides or trimethylsilylamide salts of Co or Fe. These catalysts are regarded as having reactivity to only phenyltrihydrosilane, but not having reactivity to heptamethyltrisiloxane.

Likewise, Patent Document 25 discloses exemplary Ni compounds and carbene compounds. Only one example is regarded as having activity to addition reaction of heptamethyltrisiloxane, whereas some other examples have activity to only phenyltrihydrosilane, and many other examples have activity to neither phenyltrihydrosilane nor heptamethyltrisiloxane.

Patent Documents 23 and 26 disclose exemplary Ir or Ru compounds and carbene compounds. Of these, only metal compounds having a COD or $\eta^6$-aryl group as an olefinic ligand exhibit reactivity.

In all examples described in Patent Documents 21 to 26, ionic salts or hydride reducing agents are used as the activator. Nevertheless, almost all examples exhibit no catalytic activity.

PRIOR ART DOCUMENTS

Patent Documents

Patent Document 1: WO 2013/081794
Patent Document 2: WO 2010/016416
Patent Document 3: JP-A 2012-532885
Patent Document 4: JP-A 2012-532884
Patent Document 5: JP-A 2013-544824
Patent Document 6: JP-A 2014-502271
Patent Document 7: JP-A 2014-503507
Patent Document 8: JP-A H06-136126
Patent Document 9: JP-A H06-263780
Patent Document 10: JP-A H01-315344

Patent Document 11: JP 3174616
Patent Document 12: JP-A H07-149780
Patent Document 13: JP-A 2001-131231
Patent Document 14: JP 4007467
Patent Document 15: JP 3599669
Patent Document 16: JP 3854151
Patent Document 17: JP 4249702
Patent Document 18: JP 4934190
Patent Document 19: JP 5032561
Patent Document 20: WO 2013/043846
Patent Document 21: WO 2013/043783
Patent Document 22: WO 2013/043912
Patent Document 23: WO 2014/021908
Patent Document 24: WO 2013/081794
Patent Document 25: WO 2013/043785
Patent Document 26: WO 2013/043787
Patent Document 27: CN 102516314
Patent Document 28: US 2011/0160454
Patent Document 29: CN 102351907
Patent Document 30: WO 2008/095785
Patent Document 31: FR 2911876
Patent Document 32: U.S. Pat. No. 6,737,531
Patent Document 33: US 2004/0236054
Patent Document 34: U.S. Pat. No. 7,019,145

Non-Patent Documents

Non-Patent Document 1: A. N. Nesmeyanov et al., Tetrahedron, 1962, 17, 61
Non-Patent Document 2: M. S. Wrighton et al., J. Organomet. Chem., 1977, 128, 345
Non-Patent Document 3: F. Kakiuchi et al., J. Organomet. Chem., 1993, 456, 45
Non-Patent Document 4: H. Nakazawa et al., J. Am. Chem. Soc., 2012, 134, 804
Non-Patent Document 5: H. Nakazawa et al., Organometallics, 2012, 31, 3825
Non-Patent Document 6: P. J. Chirik et al., Organometallics, 2012, 31, 4886
Non-Patent Document 7: P. J. Chirik et al., J. Am. Chem. Soc., 2004, 126, 13794
Non-Patent Document 8: P. J. Chirik et al., Science, 2012, 335, 567
Non-Patent Document 9: A. J. Chalk et al., J. Am. Chem. Soc., 1965, 87, 1133
Non-Patent Document 10: A. J. Chalk et al., J. Am. Chem. Soc., 1967, 89 1640
Non-Patent Document 11: A. J. Chalk et al., J. Organomet. Chem., 1970, 21, 207
Non-Patent Document 12: B. A. Izmailov et al., J. Organomet. Chem., 1978, 149, 29
Non-Patent Document 13: N. Sonoda et al., J. Org. Chem., 1987, 52, 4864
Non-Patent Document 14: S. Murai et al., Chem. Lett., 2000, 14
Non-Patent Document 15: M. S. Wrighton et al., Inorg. Chem., 1980, 19, 3858
Non-Patent Document 16: B. E. Grant et al., J. Am. Chem. Soc., 1993, 115, 2151
Non-Patent Document 17: L. Deng et al., Angew. Chem. Int. Ed., 2013, 52, 10845
Non-Patent Document 18: M. Umeno et al., J. Organomet. Chem., 1973, 50, 297
Non-Patent Document 19: I. Kownacki et al., J. Organomet. Chem., 2000, 597, 175
Non-Patent Document 20: P. Valerga et al., Dalton Trans., 2007, 3000
Non-Patent Document 21: T. D. Tilley et al., Chem. Commun., 2012, 48, 7146
Non-Patent Document 22: P. Valerga et al., Organometallics, 2012, 31, 2175
Non-Patent Document 23: T. A. Nile et al., J. Organomet. Chem., 1977, 137, 293
Non-Patent Document 24: M. R. Buchmeiser et al., J. Organomet. Chem., 2005, 690, 4433
Non-Patent Document 25: X. Li et al., J. Organomet. Chem., 2011, 696, 2116
Non-Patent Document 26: S. P. Nolan et al., Dalton Trans., 2013, 42, 270
Non-Patent Document 27: J. M. Walters et al., J. Molecular Catalysis, 1985, 29, 201
Non-Patent Document 28: M. F. Lappert et al., J. Organomet. Chem., 1979, 172, 153

SUMMARY OF THE INVENTION

Problems to be Solved by the Invention

An object of the invention, which has been made under the above-mentioned circumstances, is to provide a hydrosilylation reaction catalyst which helps hydrosilylation reaction take place under mild conditions and is improved in handling and storage; and a method for preparing an addition compound by hydrosilylation reaction using the same.

Means for Solving the Problems

Making extensive investigations to attain the above objects, the inventors have found that a catalyst which is obtained using a specific metal compound as the catalyst precursor and a carbene compound as the ligand component exerts a high activity to hydrosilylation reaction and helps addition reaction take place under mild conditions. The invention is predicated on this finding.

The invention provides a catalyst and a method defined below.

1. A hydrosilylation reaction catalyst which is prepared from:
a metal salt compound having the formula (1):

$$M_a(L)_b(X)_c \quad (1)$$

wherein M is a transition metal selected from Groups 8, 9 and 10 in the Periodic Table, exclusive of platinum, X is a halogen atom, L is a monovalent organic group of at least one type selected from the formulae (3) to (5), a is an integer of 1 or 2, b is an integer of 0 to 6, c is an integer of 0 to 3, satisfying b+c=2 or 3 when a is 1, and b+c=4 to 6 when a is 2, $$—O—R^1 \quad (3)$$

$$—OCO—R^1 \quad (4)$$

$$—OSO_2—R^1 \quad (5)$$

wherein $R^1$ is each independently an optionally substituted, $C_1$-$C_{30}$ monovalent organic group which may be separated by at least one atom selected from oxygen, nitrogen, sulfur and phosphorus, or a monovalent organic group having the formula (6):

$$-(A)_p-R^2 \quad (6)$$

wherein A is a $C_1$-$C_{30}$ divalent organic group which may be substituted with halogen, p is an integer of 0 or 1, satisfying p=0 or 1 when L is a monovalent organic group having formula (3), and p=1 when L is a monovalent organic group having formula (4) or (5), $R^2$ is a group having the formula (7):

$$-\{Si(R^3)_2-R^4\}_s-Si(R^3)_d\{[(OSi(R^3)_2)]_f-R^3\}_e \quad (7)$$

wherein $R^3$ is each independently an optionally substituted, $C_1$-$C_{20}$ alkyl group, $C_1$-$C_{20}$ alkoxy group, $C_6$-$C_{20}$ aryl group or $C_7$-$C_{20}$ aralkyl group which may be separated by at least one atom selected from oxygen, nitrogen, sulfur and phosphorus, $R^4$ is a $C_1$-$C_{10}$ divalent hydrocarbon group, s is an integer of 0 or 1, d is an integer of 0 to 3, e is an integer of 0 to 3, satisfying d+e=3, and f is an integer of 1 to 300, and a carbene compound having one or two adjoining nitrogen atoms, represented by the formula (2):

[Chemical Formula 1]

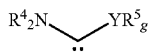
(2)

wherein Y is a carbon, nitrogen or oxygen atom, g is 3 when Y is carbon, g is 2 when Y is nitrogen, g is 1 when Y is oxygen, $R^4$ and $R^5$ are each independently a $C_1$-$C_{30}$ alkyl, aryl or aralkyl group which may be substituted with a halogen atom or alkoxy group, and any one of $R^4$ and any one of $R^5$ may bond together to form a divalent organic group so that the compound has a cyclic structure, which may contain a nitrogen atom and/or unsaturated bond.
2. The hydrosilylation reaction catalyst of 1 wherein in formula (7), s is 0.
3. The hydrosilylation reaction catalyst of 1 or 2 wherein a is 1 or 2, b is 2 to 4, and c is 0 to 1, b+c=2 when a is 1, and b+c=4 or 5 when a is 2.
4. The hydrosilylation reaction catalyst of any one of 1 to 3 which is prepared in a system where hydrosilylation reaction of a compound having an aliphatic unsaturated bond with a hydrosilane compound having a Si—H group or organohydropolysiloxane compound is carried out.
5. The hydrosilylation reaction catalyst of any one of 1 to 4 wherein the carbene compound of formula (2) has the formula (8):

[Chemical Formula 2]

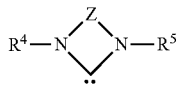
(8)

wherein Z is a $C_2$-$C_5$ divalent organic group which may contain a nitrogen atom and/or unsaturated bond, $R^4$ and $R^5$ are each independently a $C_1$-$C_{30}$ alkyl, aryl or aralkyl group which may be substituted with a halogen atom or alkoxy group.
6. The hydrosilylation reaction catalyst of any one of 1 to 5 wherein M is Fe, Co or Ni, a is 1, b is 2, and c is 0.
7. The hydrosilylation reaction catalyst of any one of 1 to 5 wherein M is Rh, a is 2, b is 4, and c is 0.
8. The hydrosilylation reaction catalyst of any one of 1 to 5 wherein M is Ru, a is 2, b is 4, and c is 1.
9. The hydrosilylation reaction catalyst of any one of 1 to 8 wherein L is a monovalent organic group having formula (4).
10. A method for preparing an addition compound comprising the step of carrying out hydrosilylation reaction of a compound having an aliphatic unsaturated bond with a hydrosilane compound having a Si—H group or organohydropolysiloxane compound in the presence of the hydrosilylation reaction catalyst of any one of 1 to 9.
11. The method for preparing an addition compound of 10 wherein the compound having an aliphatic unsaturated bond is an organopolysiloxane having an alkenyl group.

Advantageous Effects of the Invention

The metal compound from which the hydrosilylation reaction catalyst of the invention is prepared is readily available as a commercial product or synthesized by a well-known method.

Also, since the inventive catalyst is free of such a ligand as carbonyl, $\eta^4$-diene, $\eta^5$-cyclopentadienyl, $\eta^6$-arene or $\eta^6$-triene group, it is quite easy to handle without a need for storage at a low temperature or in an inert gas atmosphere or for weighing or handling in a glove box, and has the advantage that it maintains high reactivity even after long-term exposure to air.

On the other hand, the carbene compound serving as the ligand component may also be stored at room temperature and eliminates a need for a special equipment for handling.

In order to use a metal compound to generate a reactive species, generally a reducing agent capable of reducing a high valence metal species in a system must be added. According to the invention, the desired addition reaction by hydrosilylation takes place without a need to add a reducing agent because the reactant, hydrosilane itself is utilized as the reducing agent.

The catalyst prepared from the metal compound and carbene compound may be used after isolation as a metal complex compound or it may be prepared in situ in a hydrosilylation reaction system and used without isolation.

If hydrosilylation reaction between a compound containing an aliphatic unsaturated group and a silane having a Si—H group or polysiloxane is carried out in the presence of the catalyst prepared from the metal compound and carbene compound, addition reaction is possible under such conditions as room temperature to 100° C. In particular, addition reaction with industrially useful polysiloxanes, trialkoxysilanes and dialkoxysilanes takes place effectively.

Although the cited documents describe that in the relevant reaction, addition reaction to an unsaturated group and reaction to produce an unsaturated group-containing compound by dehydrogenation silylation reaction often take place at the same time, the use of the inventive catalyst ensures selective progress of addition reaction to an unsaturated group.

In addition, with respect to the reaction with an internal olefin which is difficult with the prior art catalysts, an addition reaction product with the unsaturated group migrating to the terminus is obtainable according to the invention. The invention is thus quite useful in the silicone industry.

BRIEF DESCRIPTION OF THE DIAGRAMS

EMBODIMENT FOR CARRYING OUT THE INVENTION

Figure 1:
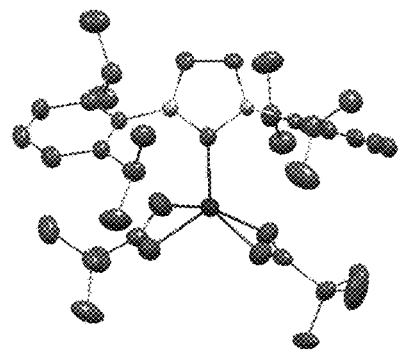
FIG. 1 is a model showing the results of x-ray crystallographic analysis on cobalt complex A obtained in Synthesis Example 5.

Below the invention is described in more detail.

The invention provides a hydrosilylation reaction catalyst which is prepared from a metal compound having the formula (1) serving as a catalyst precursor and a carbene compound having the formula (2) serving as a ligand.

$$M_a(L)_b(X)_c \tag{1}$$

[Chemical Formula 3]

$$R^4{}_2N\diagdown\diagup YR^5{}_g \tag{2}$$

In formula (1), M is a transition metal selected from Groups 8, 9 and 10 in the Periodic Table, exclusive of platinum, preferably Fe, Co, Ni, Ru, Rh, Pd, Os, and Ir. With the availability and cost of the metal salt, catalytic activity and other factors taken into account, Fe, Co, Ni, Ru, Rh, Os, and Ir are more preferred, and Fe, Co, Ru, Ni, and Rh are even more preferred.

X is a halogen atom, for example, fluorine, chlorine, bromine, and iodine atoms. Chlorine and bromine atoms are preferred, with chlorine atoms being more preferred.

L is a monovalent organic group to bond with the transition metal M via oxygen, specifically a monovalent organic group of at least one type selected from the formulae (3) to (5), preferably a monovalent organic group of formula (4).

$$-O-R^1 \tag{3}$$

$$-OCO-R^1 \tag{4}$$

$$-OSO_2-R^1 \tag{5}$$

In formulae (3) to (5), $R^1$ is each independently an optionally substituted, $C_1$-$C_{30}$ monovalent organic group which may be separated by at least one atom selected from oxygen, nitrogen, sulfur and phosphorus, or a monovalent organic group having the formula (6).

$$-(A)_p-R^2 \tag{6}$$

The $C_1$-$C_{30}$ monovalent organic groups are preferably $C_1$-$C_{30}$ monovalent hydrocarbon groups, but not limited thereto.

Suitable monovalent hydrocarbon groups include alkyl, alkenyl, alkynyl, aryl and aralkyl groups.

The alkyl groups may be straight, branched or cyclic, preferably $C_1$-$C_{20}$, more preferably $C_1$-$C_{10}$ alkyl groups. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, cyclononyl, norbornyl, and adamantyl.

The alkenyl groups are preferably $C_2$-$C_{20}$ alkenyl groups. Examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

The alkynyl groups are preferably $C_2$-$C_{20}$ alkynyl groups. Examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl, and n-1-eicosynyl.

The aryl groups are preferably $C_6$-$C_{30}$, more preferably $C_6$-$C_{20}$ aryl groups. Examples include phenyl, 1-naphthyl, 2-naphthyl, anthryl, phenanthryl, o-biphenylyl, m-biphenylyl, and p-biphenylyl.

The aralkyl groups are preferably $C_7$-$C_{30}$, more preferably $C_7$-$C_{20}$ aralkyl groups. Examples include benzyl, phenylethyl, phenylpropyl, naphthylmethyl, naphthylethyl, and naphthylpropyl.

In these groups, one or more atoms selected from oxygen, nitrogen, sulfur and phosphorus may intervene as long as the activity of the inventive hydrosilylation reaction catalyst is not impaired.

The $C_1$-$C_{30}$ monovalent organic group may have a substituent or a plurality of identical or different substituents at arbitrary positions.

Examples of the substituent include halogen atoms such as fluorine and chlorine, alkoxy groups such as methoxy, ethoxy and propoxy, and amino groups such as dialkylamino groups.

In formula (6), A is an optionally substituted, $C_1$-$C_{30}$ divalent organic group which may be separated by at least one atom selected from oxygen, nitrogen, sulfur and phosphorus, p is an integer of 0 or 1, satisfying p=0 or 1 when L is a monovalent organic group having formula (3), and p=1 when L is a monovalent organic group having formula (4) or (5).

The $C_1$-$C_{30}$ divalent organic groups are preferably $C_1$-$C_{30}$ divalent hydrocarbon groups, but not limited thereto.

Suitable divalent hydrocarbon groups include alkylene, arylene and aralkylene groups.

The alkylene groups may be straight, branched or cyclic, preferably $C_1$-$C_{20}$, more preferably $C_1$-$C_{10}$ alkylene groups. Examples include straight or branched alkylene groups such as methylene, ethylene, propylene, trimethylene, n-butylene, isobutylene, s-butylene, n-octylene, 2-ethylhexylene, n-decylene, n-undecylene, n-dodecylene, n-tridecylene, n-tetradecylene, n-pentadecylene, n-hexadecylene, n-heptadecylene, n-octadecylene, n-nonadecylene, and n-eicosanylene; and cycloalkylene groups such as 1,4-cyclohexylene.

The arylene groups are preferably $C_6$-$C_{30}$, more preferably $C_6$-$C_{20}$ arylene groups. Examples include o-phenylene, m-phenylene, p-phenylene 1,2-naphthylene, 1,8-naphthylene, 2,3-naphthylene, and 4,4'-biphenylene.

The aralkylene groups are preferably $C_7$-$C_{30}$, more preferably $C_7$-$C_{20}$ aralkylene groups. Examples include —$(CH_2)_k$—Ar— wherein Ar is a $C_6$-$C_{20}$ arylene group and k is an integer of 1 to 10, —Ar—$(CH_2)_k$— wherein Ar and k are as defined above, and —$(CH_2)_k$—Ar—$(CH_2)_k$— wherein Ar is as defined above and k is each independently as defined above.

$R^2$ is a silyl or polyorganosiloxane group having the formula (7).

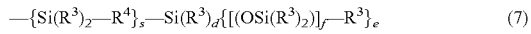
$$—\{Si(R^3)_2—R^4\}_s—Si(R^3)_d\{[(OSi(R^3)_2)]_f—R^3\}_e \quad (7)$$

In formula (7), $R^3$ is an optionally substituted, $C_1$-$C_{30}$ alkyl group, alkoxy group, aryl group or aralkyl group which may be separated by at least one atom selected from oxygen, nitrogen, sulfur and phosphorus, and $R^4$ is a $C_1$-$C_{10}$ divalent hydrocarbon group.

The $C_1$-$C_{30}$ alkoxy groups are preferably $C_1$-$C_{10}$ alkoxy groups. Examples include methoxy, ethoxy, n-propoxy, i-propoxy, n-butoxy, i-butoxy, s-butoxy, t-butoxy, n-pentoxy, n-hexoxy, n-heptyloxyl, n-octyloxy, n-nonyloxy, and n-decyloxy.

Suitable alkyl, aryl and aralkyl groups are as exemplified above for $R^1$.

Examples of the substituent include halogen atoms such as fluorine and chlorine, alkoxy groups such as methoxy, ethoxy and propoxy, and amino groups such as dialkylamino groups.

Examples of the $C_1$-$C_{10}$ divalent hydrocarbon group represented by $R^4$ include alkylene groups such as ethylene and propylene, preferably ethylene.

The subscript s is an integer of 0 or 1, d is an integer of 0 to 3, e is an integer of 0 to 3, satisfying d+e=3, and f is an integer of 1 to 300. Preferred is a silyl or polyorganosiloxane group having the formula (7') corresponding to formula (7) wherein s=0.

$$—Si(R^3)_d\{[(OSi(R^3)_2)]_f—R^3\}_e \quad (7')$$

Examples of the silyl or polyorganosiloxane group having formula (7) include, but are not limited to, trimethylsilyl, triethylsilyl, phenyldimethylsilyl, trimethoxysilyl, triethoxysilyl, pentamethyldisiloxy, bistrimethylsiloxymethylsilyl, tristrimethylsiloxysilyl, polydimethylsiloxy groups of the formula: —Si(Me)$_2${OSi(Me)$_2$}$_{f-1}$-OSiMe$_3$ wherein f is as defined above, and polydimethylsiloxy groups of the formula: —Si(Me)$_2${OSi(Me)$_2$}$_{f-1}$-OSiMe$_2$nBu wherein f is as defined above.

Besides the groups of formula (7), $R^2$ may be a siloxane group of dendrimer type which is highly branched via silethylene groups.

Of the foregoing, $R^1$ is preferably an optionally halo-substituted, $C_1$-$C_{30}$ monovalent hydrocarbon group, more preferably an optionally halo-substituted, $C_1$-$C_{10}$ alkyl group, and even more preferably an optionally halo-substituted, $C_1$-$C_5$ alkyl group.

In formula (1), a is 1 or 2, b is an integer of 0 to 6, and c is an integer of 0 to 3, which are selected in accordance with the valence number of metal M so as to satisfy b+c=2 or 3 when a is 1, and b+c=4 to 6 when a is 2. Preferably b is 2 to 4.

Specifically, when M in formula (1) is Fe, Co or Ni, preferably a is 1, b is 2 or 0, and c is 0, 2 or 3; more preferably a is 1, b is 2, and c is 0.

When M in formula (1) is Rh, preferably a is 2, b is 4, and c is 0.

When M in formula (1) is Ru, preferably a is 2, b is 4, and c is 1.

Examples of the metal compound which may be preferably used herein as the catalyst precursor include, but are not limited to, iron compounds such as iron(II) acetate, iron(II) pivalate, iron(II) trifluoroacetate (tetrahydrofuran complex, referred to as THF hereinafter), and iron-oxygen bond-bearing iron complexes prepared from [Fe(mesityl)(μ-mesityl)]$_2$ and alcohols, carboxylic acids or siloxane-containing carboxylates; cobalt compounds such as cobalt(II) acetate, cobalt(II) chloride, cobalt(II) bromide, cobalt(II) isopropoxide, cobalt(II) pivalate, and cobalt(II) trifluoroacetate (THF); nickel compounds such as nickel(II) acetate and nickel(II) pivalate; ruthenium compounds such as Ru$_2$(μ-OAc)$_4$Cl; and rhodium compounds such as rhodium(II) acetate dimer.

It is noted that these metal salts may be obtained as commercial products or synthesized by the methods described in the literature (J. Cluster Sci., 2005, 16, 331; Inorganic Chemistry, 2007, 46, 3378; Organometallics, 1993, 12, 2414; Russ. Chem. Bull., 1999, 48, 1751; J. Inorg. Nucl. Chem., 1966, 28, 2285, etc.).

On the other hand, the ligand of formula (2) is a carbene compound having one or two adjoining nitrogen atoms.

In formula (2), Y is a carbon, nitrogen or oxygen atom, g is 3 when Y is carbon, g is 2 when Y is nitrogen, and g is 1 when Y is oxygen.

$R^4$ and $R^5$ are each independently a $C_1$-$C_{30}$ alkyl, aryl or aralkyl group which may be substituted with a halogen atom or alkoxy group, and any one of $R^4$ and any one of $R^5$ may bond together to form a divalent organic group so that the compound has a cyclic structure, which may contain a nitrogen atom and/or unsaturated bond.

Examples of the $C_1$-$C_{30}$ alkyl, aryl and aralkyl groups and alkoxy groups are as exemplified above.

Preferred are cyclic carbene compounds having the formula (8).

[Chemical Formula 4]

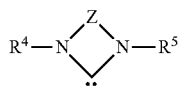

(8)

Herein Z is a $C_2$-$C_5$ divalent organic group which may contain a nitrogen atom and/or unsaturated bond. Examples include vinylene and prop-1-ene-1,3-diyl (propenylene) in addition to the $C_2$-$C_5$ groups exemplified above for the $C_1$-$C_{30}$ divalent organic group.

Suitable cyclic carbene compounds include the following compounds, but are not limited thereto.

[Chemical Formula 5]

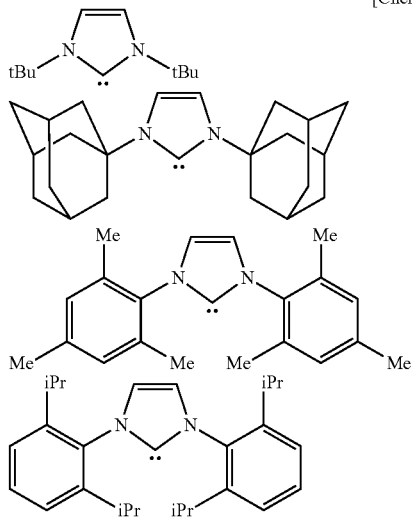

-continued

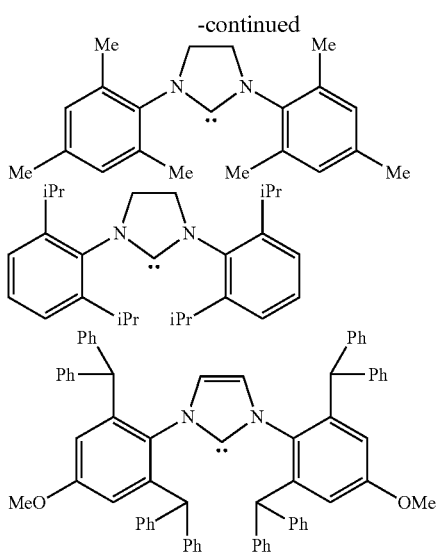

Besides, hydrosilylation reaction may be performed while an imidazolium salt as a precursor is reacted with a base such as KOtBu to generate a carbene compound in the system.

Suitable imidazolium salts as a precursor include the following compounds, but are not limited thereto.

[Chemical Formula 6]

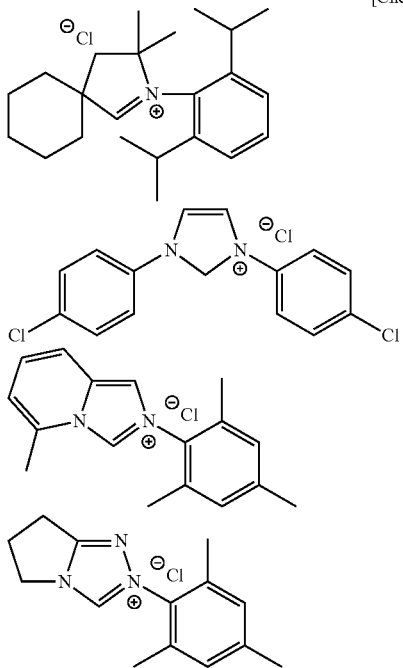

Notably, a well-known two-electron donative ligand may be used in combination with the inventive hydrosilylation reaction catalyst as long as the activity of the catalyst is not impaired. Although the two-electron donative ligand is not particularly limited, ligands other than carbonyl are preferred, for example, ammonia molecules, ether compounds, amine compounds, phosphine compounds, phosphite compounds, and sulfide compounds.

In preparing the inventive hydrosilylation reaction catalyst, the amounts of the metal compound and the carbene compound used are not particularly limited. Preferably the carbene compound is used in an amount of about 0.5 to 10 equivalents, more preferably 1 to 6 equivalents, and even more preferably 2 to 4 equivalents per equivalent of the metal compound.

When hydrosilylation reaction is carried out in the presence of the inventive hydrosilylation reaction catalyst, the amount of the catalyst used is not particularly limited. In order that the reaction take place under mild conditions of the order of room temperature to 100° C. to form the desired product in high yields, the catalyst is preferably used in an amount of at least 0.1 mol %, more preferably at least 0.5 mol % of metal compound per mole of the substrate, aliphatic unsaturated bond-containing compound.

Although no upper limit is imposed on the amount of metal compound used, the upper limit is preferably about 10 mol %, more preferably 5 mol % per mole of the substrate, as viewed from the economic standpoint.

The inventive hydrosilylation reaction catalyst may be used after isolation from a metal complex catalyst prepared from the metal compound and the carbene compound. In an alternative embodiment, the catalyst may be prepared from the metal compound and the carbene compound in a system where hydrosilylation reaction of a compound having an aliphatic unsaturated bond with a hydrosilane compound having a Si—H group or organohydropolysiloxane compound is carried out. The latter embodiment wherein the catalyst is prepared in situ and used without isolation is preferable from the standpoint of convenience of operation.

In this embodiment, once the catalyst is prepared from the metal compound and the carbene compound, the compound having an aliphatic unsaturated bond and the hydrosilane compound having a Si—H group or organohydropolysiloxane compound may be added thereto, or separate sets of some components may be fed, or all components may be fed at a time.

Although the reaction conditions for the metal compound and the carbene compound are not particularly limited, generally the reaction temperature is about 10 to about 100° C., preferably 30 to 80° C. and the reaction time is about 1 to about 48 hours.

Although an organic solvent may be used during catalyst preparation and hydrosilylation reaction, the invention favors a solventless or neat system.

The organic solvent, if used, may be of any type as long as the reaction is not affected. Examples include aliphatic hydrocarbons such as pentane, hexane, heptane, octane, and cyclohexane, ethers such as diethyl ether, diisopropyl ether, dibutyl ether, cyclopentyl methyl ether, tetrahydrofuran and 1,4-dioxane; and aromatic hydrocarbons such as benzene, toluene, xylene, and mesitylene.

In conducting hydrosilylation reaction using the inventive hydrosilylation reaction catalyst, as long as a compound having an aliphatic unsaturated bond such as an olefin, silane or organopolysiloxane compound having an aliphatic unsaturated bond and a silane or organopolysiloxane compound having a Si—H bond are used in combination, no limit is imposed on the structure of the respective compounds.

The hydrosilylation reaction using the inventive hydrosilylation reaction catalyst is applicable to all applications which are industrially implemented using prior art platinum catalysts, including silane coupling agents obtained from an olefin compound having an aliphatic unsaturated bond and a silane compound having a Si—H bond, and modified silicone oils obtained from an olefin compound having an aliphatic unsaturated bond and an organopolysiloxane having a Si—H bond, as well as silicone cured products obtained from an organopolysiloxane compound having an aliphatic unsaturated bond and an organopolysiloxane having a Si—H bond.

EXAMPLES

Synthesis Examples and Examples are given below by way of illustration and not by way of limitation.

For synthesis of complexes, a Schlenk system or glovebox was used, and all steps were performed in nitrogen or argon atmosphere. All solvents were deoxygenated and dehydrated by well-known methods before they were used in the preparation of metal compounds.

The metal compounds obtained were stored in a nitrogen gas atmosphere at 25° C. before they were used in reaction.

Hydrosilylation reaction and solvent purification of alkenes were always carried out in an inert gas atmosphere. The solvents and other ingredients were purified, dried and deoxygenated by well-known methods before they were used in various reactions.

Analyses of $^1$H and $^{13}$C-NMR spectroscopy were performed by JNM-ECA 600 and JNM-LA 400 of JEOL Ltd., IR spectroscopy by FT/IR-550 of JASCO Corp., elemental analysis by 2400II/CHN of Perkin Elmer, x-ray crystallography analysis by VariMax (MoK α-ray 0.71069 angstrom) of Rigaku Corp.

It is understood that hydrogen atoms are omitted from the chemical structural formula, shown below, according to the conventional expression. OAc stands for an acetate anion, iPr for isopropyl, and NHC for N-heterocyclic carbene ligand.

Synthesis of Metal Compounds

Synthesis Example 1

Synthesis of Iron Pivalate

With reference to J. Cluster Sci., 2005, 16, 331, the compound was synthesized by the following procedure.

A 50 mL two-neck recovery flask equipped with a reflux tube was charged with 0.86 g (15.4 mmol) of reduced iron and 3.50 g (34.3 mmol) of pivalic acid, which were stirred at 160° C. for 12 hours. On this occasion, the reaction solution turned from colorless clear to green. Further 2.50 g (24.5 mmol) of pivalic acid was added to the solution, which was stirred at 160° C. for 19 hours. Thereafter, the reaction solution was filtered, and the filtrate was combined with the recovered supernatant and dried in vacuum at 80° C. The resulting solid was washed with hexane, obtaining a green solid (2.66 g, yield 67%).

FT-IR (KBr) ν: 2963, 2930, 2868, 1583, 1523, 1485, 1457, 1427, 1379, 1362, 1229, 1031, 938, 900, 790, 608, 576, 457 cm$^{-1}$

Synthesis Example 2

Preparation of Iron Precursor Having Iron-Oxygen Bond Using [(Fe(mesityl)(μ-mesityl)]$_2$ With reference to Organometallics, 1993, 12, 2414, the compound was synthesized by the following procedure.

A 50 mL two-neck recovery flask was charged with 1.08 g (44.3 mmol) of magnesium ribbon and 35 mL of THF, after which 8.49 g (42.6 mmol) of bromomesitylene was slowly added dropwise. It was confirmed that exotherm ceased at the end of dropwise addition, after which the reaction solution was stirred at 60° C. for 3 hours. The solution was filtered through a glass filter, obtaining a THF solution of mesitylmagnesium bromide Grignard reagent.

A 100 mL Schlenk flask was charged with 2.63 g (20.7 mmol) of FeCl$_2$, 30 mL of THF, and 10 mL of 1,4-dioxane and cooled down to −78° C. The THF solution of mesitylmagnesium bromide Grignard reagent was slowly added to the flask, followed by stirring at 25° C. for 2 hours. On this occasion, the reaction solution turned from a brown suspension to a red suspension. Thereafter, the precipitated solid was separated by centrifugation and dried in vacuum. The resulting red solid was dissolved in diethyl ether, after which the solid was separated again by centrifugation and recrystallized at −30° C., obtaining a crystal (4.36 g, yield 72%). The crystal was identified by $^1$H-NMR analysis in C$_6$D$_6$.

$^1$H-NMR (600 MHz, C$_6$D$_6$) δ: 23.68 (s, 2H), 23.17 (s, 2H), 21.44 (s, 3H), 17.94 (s, 3H), 10.19 (s, 6H), −6.66 (s, 6H)

In a 20 mL Schlenk flask, 3 mg (0.01 mmol) or 9 mg (0.015 mmol) of the thus obtained [(Fe(mesityl)(μ-mesityl)]$_2$ was dissolved in 1 mL of THF. To the solution, 16 mg (0.09 mmol) of 1,1,1,3,3,3-hexafluoroisopropanol was added, followed by stirring at 25° C. for 30 minutes. This was followed by vacuum drying, obtaining an iron precursor having an iron-oxygen bond (Fe(OR)$_2$).

Synthesis Example 3

Synthesis of Cobalt Pivalate

With reference to Russ. Chem. Bull., 1999, 48, 1751, the compound was synthesized by the following procedure.

A 50 mL two-neck recovery flask equipped with a reflux tube was charged with 1.15 g (6.5 mmol) of cobalt acetate, 1.55 g (15.2 mmol) of pivalic acid, and 0.5 mL (2.5 mmol) of pivalic anhydride, which were stirred at 160° C. for 1 hour. On this occasion, the reaction solution turned from thin purple to purple. Thereafter, the reaction solution was vacuum dried at 80° C. The resulting solid was washed with pentane and diethyl ether and dried, obtaining a purple solid (1.15 g, yield 68%).

FT-IR (KBr) ν: 2963, 2929, 2868, 1599, 1524, 1485, 1457, 1420, 1379, 1363, 1229, 1032, 938, 900, 792, 613, 585, 460 cm$^{-1}$

Synthesis Example 4

Synthesis of Ru$_2$(μ-OAc)$_4$Cl

With reference to J. Inorg. Nucl. Chem., 1966, 28, 2285, the compound was synthesized by the following procedure.

A 200 mL two-neck recovery flask was charged with 1.09 g (4.18 mmol) of RuCl$_3$ trihydrate, 35 mL of glacial acetic acid, and 7 mL of acetic anhydride, which were stirred at 145° C. for 2 hours. The reaction solution was cooled, once filtered, and stirred again at 145° C. for 6 hours. Then the reaction product was crystallized at −30° C., and washed with glacial acetic acid, methanol and diethyl ether, obtaining a reddish brown solid (61 mg, yield 6%).

FT-IR (KBr) ν: 3023, 2991, 2934, 1643, 1444, 1401, 1356, 1041, 1015, 944, 691, 625, 606 cm$^{-1}$

Synthesis Example 5

Synthesis of Cobalt Complex A

Figure 2:
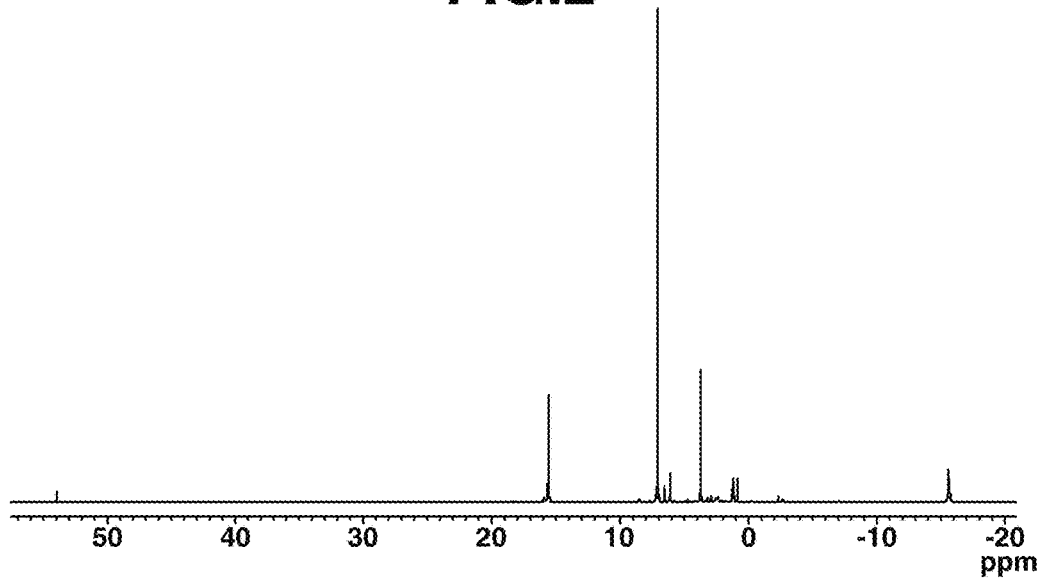
FIG. 2 is a diagram of the $^1$H-NMR spectrum of cobalt complex A in Synthesis Example 5.

A 20 mL Schlenk flask was charged with 0.20 g (0.77 mmol) of cobalt pivalate in Synthesis Example 3, 0.60 g (1.53 mmol) of 1,3-bis(2,6-diisopropylphenyl)imidazol-2-ylidene (abbreviated as IPr, hereinafter) and 20 mL of toluene, which were stirred at 25° C. for 12 hours. Then the solvent was distilled off in vacuum, followed by extraction with a diethyl ether/hexane mixture (10 mL/10 mL). The solution was vacuum concentrated to about 5 mL and recrystallized at −30° C., obtaining a clear crystal (0.20 g, yield 40%). The result of x-ray crystallography analysis on cobalt complex A is depicted in FIG. 1 and $^1$H-NMR spectrum is shown in FIG. 2.

FT-IR (KBr) ν: 3158, 3123, 3077, 2962, 2924, 2871, 1586, 1565 [ν(COCtBu$_3$-κ$^2$)], 1549, 1530, 1482, 1463, 1447, 1413, 1358, 1331, 1258, 1222, 1181, 1117, 1100, 1061, 1028, 947, 938, 900, 807, 793, 752, 695, 610, 546, 536 cm$^{-1}$ $^1$H-NMR (600 MHz, CDCl$_3$) δ: −15.59 (s, 12H), 2.54 (br, 4H), 3.78 (s, 12H), 6.16 (br, 4H), 6.55 (br, 2H), 15.64 (s, 18H), 53.88 (s, 2H)

Synthesis Example 6

Synthesis of Iron Complex B

Figure 3:
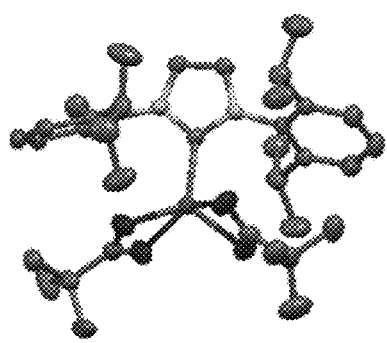
FIG. 3 is a model showing the results of x-ray crystallographic analysis on iron complex B obtained in Synthesis Example 6.
Figure 4:
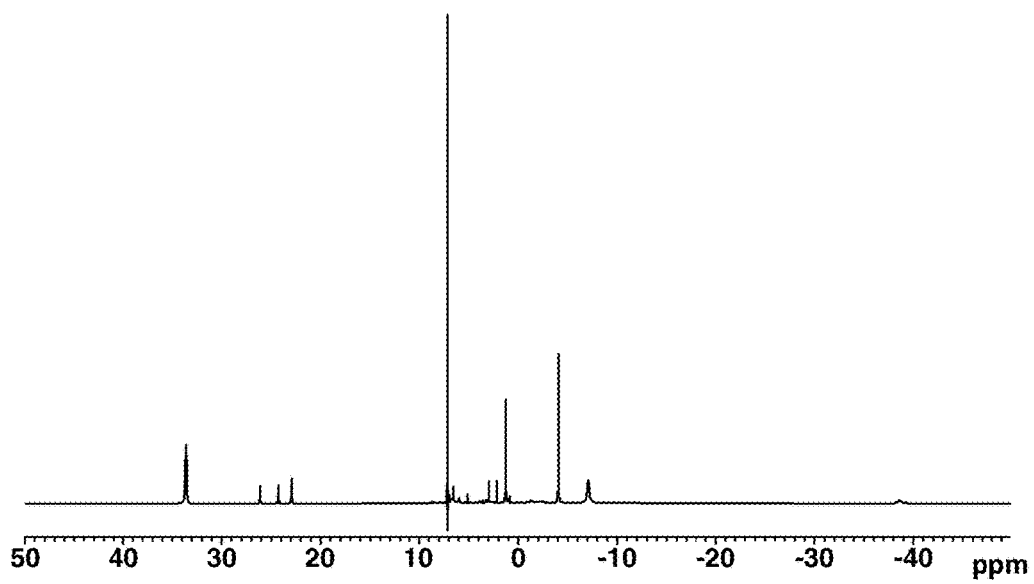
FIG. 4 is a diagram of the $^1$H-NMR spectrum of iron complex B in Synthesis Example 6.

A 20 mL Schlenk flask was charged with 0.10 g (0.39 mmol) of iron pivalate in Synthesis Example 1, 0.18 g (0.46 mmol) of IPr, and 10 mL of toluene, which were stirred at 25° C. for 12 hours. Then hexane was added, followed by extraction. The solution was vacuum concentrated to about 5 mL and recrystallized at −30° C., obtaining a clear crystal (0.06 g, yield 26%). The result of x-ray crystallography analysis on iron complex B is depicted in FIG. 3 and $^1$H-NMR spectrum is shown in FIG. 4.

$^1$H-NMR (600 MHz, CDCl$_3$) δ: −38.68 (br, 4H), −7.07 (br, 12H), −4.05 (s, 12H), 22.99 (s, 4H), 24.32 (s, 2H), 26.18 (s, 2H), 33.68 (s, 18H)

(1) Hydrosilylation of 1-octene with 1,1,3,3,3-pentamethyldisiloxane Using Complex Having Metal-oxygen Bond and NHC Ligand

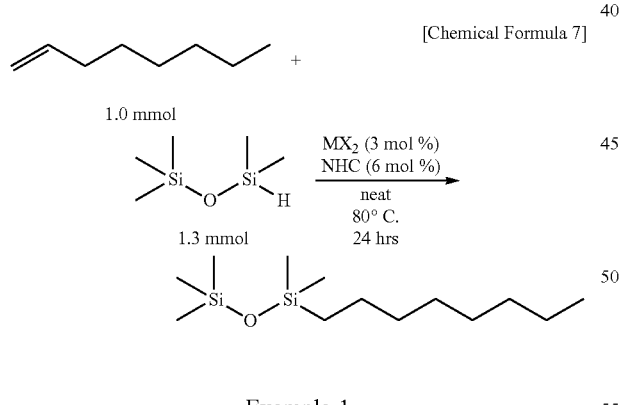

[Chemical Formula 7]

Example 1

Hydrosilylation Using Iron Pivalate and 1,3-dimesitylimidazol-2-ylidene (Abbreviated as IMes, Hereinafter)

A screw-top vial was charged with 8 mg (0.03 mmol) of iron pivalate in Synthesis Example 1 as a catalyst precursor, 18 mg (0.06 mmol) of IMes as a NHC ligand, 254 μL (1.3 mmol) of 1,1,3,3,3-pentamethyldisiloxane, and 157 μL (1.0 mmol) of 1-octene. The vial was closed, after which the contents were stirred at 80° C. for 24 hours. Thereafter, 1.0 mmol of anisole as an internal standard was added to the reaction solution and stirred. A minute amount of the solution was dissolved in deuterochloroform, passed through alumina to remove the catalyst, and analyzed by $^1$H-NMR spectroscopy. In the following Examples, a test sample was prepared according to the same procedure and analyzed by $^1$H-NMR spectroscopy. As a result, it was confirmed that the signal assigned to the ethylene site of 1-octene as the reactant disappeared completely. Instead, a multiplet at 0.51 ppm indicative of the signal assigned to proton on silicon-adjoining carbon in the desired product, 1,1,1,3,3-pentamethyl-3-octyldisiloxane was observed, from which a yield was computed. The results are shown in Table 1. The yield computed from the $^1$H-NMR data was 65%.

Example 2

Hydrosilylation Using Iron Complex Having Iron-oxygen Bond and IMes

First, in accordance with the procedure of Synthesis Example 2, an iron precursor having an iron-oxygen bond (Fe(OR)$_2$) was prepared from 9 mg (0.015 mmol) of [Fe(mesityl)(μ-mesityl)]$_2$ and 16 mg (0.09 mmol) of 1,1,1,3,3,3-hexafluoroisopropanol. To the reactor, 18 mg (0.06 mmol) of IMes, 254 μL (1.3 mmol) of 1,1,3,3,3-pentamethyldisiloxane and 157 μL (1.0 mmol) of 1-octene were added. The reactor was closed, after which the contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.51 ppm indicative of the signal assigned to the desired product was observed, from which a yield was computed. The yield computed from the $^1$H-NMR data was 15%.

Example 3

Change of Metal Compound from Example 1

Reaction was carried out according to the same procedure as in Example 1 aside from using 5 mg (0.03 mmol) of cobalt acetate (commercial product) instead of iron pivalate. As a result, it was confirmed that the signal assigned to the reactant disappeared completely. Instead, a multiplet at 0.51 ppm indicative of the signal assigned to the desired product was observed, from which a yield was computed. The results are shown in Table 1. The yield computed from the $^1$H-NMR data was 78%.

Example 4

Change of Ligand from Example 3

Reaction was carried out according to the same procedure as in Example 3 aside from using 23 mg (0.06 mmol) of IPr instead of IMes. As a result, it was confirmed that the signal assigned to the reactant disappeared completely. Instead, a multiplet at 0.51 ppm indicative of the signal assigned to the desired product was observed, from which a yield was computed. The results are shown in Table 1. The yield computed from the $^1$H-NMR data was at least 99%.

Example 5

Change of Ligand from Example 3

Reaction was carried out according to the same procedure as in Example 3 aside from using 23 mg (0.06 mmol) of 1,3-bis(2,6-diisopropylphenyl)imidazolidin-2-ylidene instead of IMes. As a result, it was confirmed that the signal assigned to the reactant disappeared completely. Instead, a multiplet at 0.51 ppm indicative of the signal assigned to the desired product was observed, from which a yield was computed. The results are shown in Table 1. The yield computed from the $^1$H-NMR data was 58%.

Example 6

Change of Ligand from Example 3

Reaction was carried out according to the same procedure as in Example 3 aside from using 11 mg (0.06 mmol) of 1,3-di-t-butylimidazol-2-ylidene instead of IMes. As a result, it was confirmed that the signal assigned to the reactant diminished. Instead, a multiplet at 0.51 ppm indicative of the signal assigned to the desired product was observed, from which a yield was computed. The results are shown in Table 1. The conversion and yield computed from the $^1$H-NMR data were 60% and 19%, respectively.

Example 7

Change of Metal Compound from Example 3

Reaction was carried out according to the same procedure as in Example 3 aside from using 8 mg (0.03 mmol) of cobalt pivalate in Synthesis Example 3 instead of cobalt acetate. As a result, it was confirmed that the signal assigned to the reactant disappeared completely. Instead, a multiplet at 0.51 ppm indicative of the signal assigned to the desired product was observed, from which a yield was computed. The results are shown in Table 1. The yield computed from the $^1$H-NMR data was at least 99%.

Example 8

Change of Metal Compound from Example 6

Reaction was carried out according to the same procedure as in Example 6 aside from using 7 mg (0.015 mmol) of rhodium acetate dimer (commercial product), instead of cobalt acetate. As a result, it was confirmed that the signal assigned to the ethylene site of 1-octene as the reactant disappeared completely. Instead, a multiplet at 0.51 ppm indicative of the signal assigned to proton on silicon-adjoining carbon in the desired product, 1,1,1,3,3-pentamethyl-3-octyldisiloxane was observed. The yield computed from the $^1$H-NMR data was at least 99%.

Example 9

Hydrosilylation Using Cobalt Pivalate in Air Storage and IMes

A screw-top vial with a stirrer was charged with 8 mg (0.03 mmol) of cobalt pivalate in Synthesis Example 3, which was exposed to air (25° C., 60% RH) for one day. Thereafter, 18 mg (0.06 mmol) of IMes, 254 µL (1.3 mmol) of 1,1,3,3,3-pentamethyldisiloxane and 157 µL (1.0 mmol) of 1-octene were added. The vial was purged with nitrogen, after which the contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.51 ppm indicative of the signal assigned to the desired product was observed, from which a yield was computed. The results are shown in Table 1. The yield computed from the $^1$H-NMR data was at least 99%.

TABLE 1

| | Catalyst (MX$_2$) | NHC ligand (NHC) | Yield (%) |
|---|---|---|---|
| Example 1 | iron pivalate | 1,3-dimesitylimidazol-2-ylidene | 65 |
| Example 2 | Fe[OCH(CF$_3$)$_2$]$_2$ | 1,3-dimesitylimidazol-2-ylidene | 15 |
| Example 3 | cobalt acetate | 1,3-dimesitylimidazol-2-ylidene | 78 |
| Example 4 | cobalt acetate | 1,3-bis(2,6-diisopropylphenyl)imidazol-2-ylidene | >99 |
| Example 5 | cobalt acetate | 1,3-bis(2,6-diisopropylphenyl)imidazolidin-2-ylidene | 58 |
| Example 6 | cobalt acetate | 1,3-di-t-butylimidazol-2-ylidene | 19 |
| Example 7 | cobalt pivalate | 1,3-dimesitylimidazol-2-ylidene | >99 |
| Example 8 | rhodium acetate dimer | 1,3-di-t-butylimidazol-2-ylidene | >99 |
| Example 9 | cobalt pivalate (1 day storage in air) | 1,3-dimesitylimidazol-2-ylidene | >99 |

(2) Hydrosilylation of Various Alkenes with 1,1,3,3,3-pentamethyldisiloxane Using Complex Having Metal-oxygen Bond and NHC Ligand

Example 10

Hydrosilylation of Allylbenzene with 1,1,3,3,3-pentamethyldisiloxane Using Cobalt Pivalate and IMes A reactor was charged with 8 mg (0.03 mmol) of cobalt pivalate in Synthesis Example 3, 18 mg (0.06 mmol) of IMes, 254 µL (1.3 mmol) of 1,1,3,3,3-pentamethyldisiloxane, and 133 µL (1.0 mmol) of allylbenzene, which were stirred at 80° C. for 24 hours. After cooling, analysis was made by the internal standard method to find a substrate conversion of at least 99% and formation of 1,1,1,3,3-pentamethyl-3-(3-phenylpropyl)disiloxane in a yield of 30% and propylbenzene in a yield of 33%.

Example 11

Hydrosilylation of Vinyltrimethylsilane with 1,1,3,3,3-pentamethyldisiloxane Using Cobalt Pivalate and IMes A reactor was charged with 8 mg (0.03 mmol) of cobalt pivalate in Synthesis Example 3, 18 mg (0.06 mmol) of IMes, 254 µL (1.3 mmol) of 1,1,3,3,3-pentamethyldisiloxane, and 145 µL (1.0 mmol) of vinyltrimethylsilane, which were stirred at 80° C. for 24 hours. After cooling, analysis was made by the internal standard method to find a substrate conversion of at least 99% and formation of 1,1,1,3,3-pentamethyl-3-(2-trimethylsilylethyl)disiloxane in a yield of 20% and a dehydrogenated product, 1,1,1,3,3-pentamethyl-3-(2-trimethylsilylethenyl)disiloxane in a yield of 15%.

Example 12

Hydrosilylation of 2-norbornene with 1,1,3,3,3-pentamethyldisiloxane Using Cobalt Pivalate and IMes A reactor was charged with 8 mg (0.03 mmol) of cobalt pivalate in Synthesis Example 3, 18 mg (0.06 mmol) of IMes, 254 μL (1.3 mmol) of 1,1,3,3,3-pentamethyldisiloxane, and 94 mg (1.0 mmol) of 2-norbornene, which were stirred at 80° C. for 24 hours. After cooling, analysis was made by the internal standard method to find a substrate conversion of at least 99% and formation of 1-(1,1,3,3,3-pentamethyldisiloxanyl)-2-norbornene in a yield of 80%.

Example 13

Hydrosilylation of 1,7-octadiene with 1,1,3,3,3-pentamethyldisiloxane Using Cobalt Pivalate and IMes A reactor was charged with 8 mg (0.03 mmol) of cobalt pivalate in Synthesis Example 3, 18 mg (0.06 mmol) of IMes, 254 μL (1.3 mmol) of 1,1,3,3,3-pentamethyldisiloxane, and 151 μL (1.0 mmol) of 1,7-octadiene, which were stirred at 80° C. for 24 hours. After cooling, analysis was made by the internal standard method to find a substrate conversion of at least 99% and formation of 1,8-bis(1,1,3,3-pentamethyl-disiloxanyl)octane in a yield of 60% and an isomerized compound, octadiene in a yield of 5%.

Example 14

Hydrosilylation of 1,7-octadiene with 1,1,3,3,3-pentamethyldisiloxane Using Iron Pivalate and IMes A reactor was charged with 8 mg (0.03 mmol) of iron pivalate in Synthesis Example 1, 18 mg (0.06 mmol) of IMes, 254 μL (1.3 mmol) of 1,1,3,3,3-pentamethyldisiloxane, and 151 μL (1.0 mmol) of 1,7-octadiene, which were stirred at 80° C. for 24 hours. After cooling, analysis was made by the internal standard method to find a substrate conversion of at least 99% and formation of 1,8-bis(1,1,3,3-pentamethyl-disiloxanyl)octane in a yield of 60% and a single end hydrogenated product, octene in a yield of 40%.

Example 15

Hydrosilylation of 2-octene with 1,1,3,3,3-pentamethyldisiloxane Using Cobalt Pivalate and IMes A reactor was charged with 8 mg (0.03 mmol) of cobalt pivalate in Synthesis Example 3, 18 mg (0.06 mmol) of IMes, 254 μL (1.3 mmol) of 1,1,3,3,3-pentamethyldisiloxane, and 157 μL (1.0 mmol) of 2-octene, which were stirred at 80° C. for 24 hours. After cooling, analysis was made by the internal standard method to find a substrate conversion of at least 99% and formation of 1,1,1,3,3-pentamethyl-3-octyldisiloxane in a yield of 83%.

(3) Hydrosilylation Using Metal Complex

Example 16

Hydrosilylation of 1-octene with 1,1,3,3,3-pentamethyldisiloxane Using Cobalt Complex A A reactor was charged with 3 mg (0.005 mmol) of cobalt complex A in Synthesis Example 5, 254 μL (1.3 mmol) of 1,1,3,3,3-pentamethyldisiloxane, and 157 μL (1.0 mmol) of 1-octene, which were stirred at 80° C. for 24 hours. After cooling, analysis was made by the internal standard method to find a substrate conversion of at least 99% and formation of 1,1,1,3,3-pentamethyl-3-octyldisiloxane in a yield of 65% and an isomerized compound, internal octene in a yield of 10%.

Example 17

Hydrosilylation of 2-norbornene with 1,1,3,3,3-pentamethyldisiloxane Using Cobalt Complex A A reactor was charged with 6 mg (0.01 mmol) of cobalt complex A in Synthesis Example 5, 254 μL (1.3 mmol) of 1,1,3,3,3-pentamethyldisiloxane, and 94 mg (1.0 mmol) of 2-norbornene, which were stirred at 80° C. for 24 hours. After cooling, analysis was made by the internal standard method to find a substrate conversion of 58% and formation of 1-(bicyclo[2.2.1]hept-2-yl)-1,1,3,3,3-pentamethyldisiloxane in a yield of 26% and norbornane in a yield of 1%.

Example 18

Hydrosilylation of 2-norbornene with 1,1,3,3,3-pentamethyldisiloxane Using Cobalt Complex A A reactor was charged with 6 mg (0.01 mmol) of cobalt complex A in Synthesis Example 5, 4 mg (0.01 mmol) of IPr, 254 μL (1.3 mmol) of 1,1,3,3,3-pentamethyldisiloxane, and 94 mg (1.0 mmol) of 2-norbornene, which were stirred at 80° C. for 24 hours. After cooling, analysis was made by the internal standard method to find a substrate conversion of 40% and formation of 1-(bicyclo[2.2.1]hept-2-yl)-1,1,3,3,3-pentamethyldisiloxane in a yield of 11% and norbornane in a yield of 1%.

Example 19

Hydrosilylation of 1-octene with 1,1,3,3,3-pentamethyldisiloxane Using Iron Complex B A reactor was charged with 6 mg (0.01 mmol) of iron complex B in Synthesis Example 6, 254 μL (1.3 mmol) of 1,1,3,3,3-pentamethyldisiloxane, and 157 μL (1.0 mmol) of 1-octene, which were stirred at 80° C. for 24 hours. After cooling, analysis was made by the internal standard method to find a substrate conversion of >99% and formation of 1,1,1,3,3-pentamethyl-3-octyldisiloxane in a yield of 5% and an isomerized compound of 1-octene, internal octene in a yield of 84%.

Example 20

Hydrosilylation of 1-octene with 1,1,3,3,3-pentamethyldisiloxane Using Iron Complex B A reactor was charged with 6 mg (0.01 mmol) of iron complex B in Synthesis Example 6, 4 mg (0.01 mmol) of IPr, 254 μL (1.3 mmol) of 1,1,3,3,3-pentamethyldisiloxane, and 157 μL (1.0 mmol) of 1-octene, which were stirred at 80° C. for 24 hours. After cooling, analysis was made by the internal standard method to find a substrate conversion of >99% and formation of 1,1,1,3,3-pentamethyl-3-octyldisiloxane in a yield of 8% and an isomerized compound of 1-octene, internal octene in a yield of 82%.

(4) Hydrosilylation Reaction of 2-norbornene with Various Hydrosilanes Using Iron Pivalate and NHC Ligand

[Chemical Formula 8]

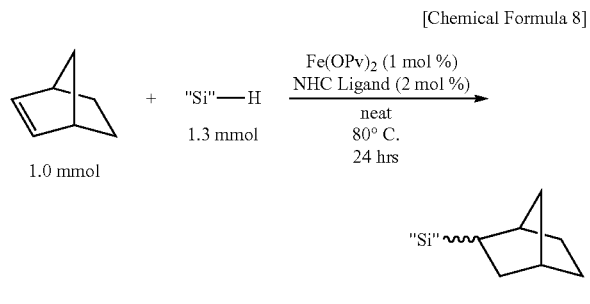

Example 21

Hydrosilylation Reaction of 2-norbornene with 1,1,3,3,3-pentamethyldisiloxane Using Iron Pivalate and IMes A screw-top vial was charged with 3 mg (0.01 mmol) of iron pivalate in Synthesis Example 1 as a catalyst, 6 mg (0.02 mmol) of IMes as a NHC ligand, 254 μL (1.3 mmol) of 1,1,3,3,3-pentamethyldisiloxane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.49 ppm indicative of the signal assigned to proton on silicon-adjoining carbon in the desired product was observed, from which a yield was computed. The results are shown in Table 2.

Example 22

Hydrosilylation Reaction of 2-norbornene with 1,1,1,3,5,5,5-heptamethyltrisiloxane Using Iron Pivalate and IMes A screw-top vial was charged with 3 mg (0.01 mmol) of iron pivalate in Synthesis Example 1 as a catalyst, 6 mg (0.02 mmol) of IMes as a NHC ligand, 353 μL (1.3 mmol) of 1,1,1,3,5,5,5-heptamethyltrisiloxane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant diminished. Instead, a multiplet at 0.45 ppm indicative of the signal assigned to proton on silicon-adjoining carbon in the desired product was observed, from which a yield was computed. The results are shown in Table 2.

Example 23

Hydrosilylation of 2-norbornene with Trimethoxysilane Using Iron Pivalate and IPr A screw-top vial was charged with 3 mg (0.01 mmol) of iron pivalate in Synthesis Example 1 as a catalyst, 8 mg (0.02 mmol) of IPr as a NHC ligand, 165 μL (1.3 mmol) of trimethoxysilane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant diminished. Instead, a multiplet at 0.76 ppm indicative of the signal assigned to proton on silicon-adjoining carbon in the desired product was observed, from which a yield was computed. The results are shown in Table 2.

TABLE 2

| | NHC ligand | Hydrosilane | Conversion (%) | Yield (%) |
|---|---|---|---|---|
| Example 21 | IMes | 1,1,3,3,3-pentamethyldisiloxane | >99 | 87 |
| Example 22 | IMes | 1,1,1,3,5,5,5-heptamethyltrisiloxane | 88 | 78 |
| Example 23 | IPr | trimethoxysilane | 49 | 42 |

(5) Hydrosilylation Reaction of 1-octene with Various Hydrosilanes Using Cobalt Pivalate and NHC Ligand

[Chemical Formula 9]

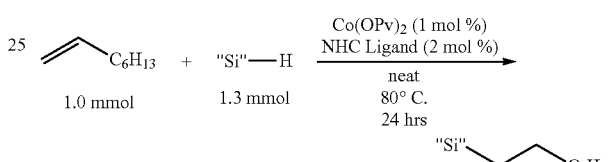

Example 24

Hydrosilylation Reaction of 1-octene with 1,1,1,3,5,5,5-heptamethyltrisiloxane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 353 μL (1.3 mmol) of 1,1,1,3,5,5,5-heptamethyltrisiloxane as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.49 ppm indicative of the signal assigned to proton on silicon-adjoining carbon in the desired product was observed, from which a yield was computed. The results are shown in Table 3.

Example 25

Hydrosilylation Reaction of Example 24 Using IPr as Ligand

Reaction was carried out according to the same procedure as in Example 24 aside from using 8 mg (0.02 mmol) of IPr instead of IMes as a ligand. As a result, it was confirmed that the signal assigned to the reactant diminished. Instead, a multiplet at 0.49 ppm indicative of the signal assigned to proton on silicon-adjoining carbon in the desired product was observed, from which a yield was computed. The results are shown in Table 3.

Example 26

Hydrosilylation Reaction of 1-octene with Ethyldimethylsilane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 165 µl, (1.3 mmol) of ethyldimethylsilane as a hydrosilane, and 157 µl, (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.47 ppm indicative of the signal assigned to proton on silicon-adjoining carbon in the desired product was observed, from which a yield was computed. The results are shown in Table 3.

Example 27

Hydrosilylation Reaction of 1-octene with Trimethoxysilane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 171 µl, (1.3 mmol) of trimethoxysilane as a hydrosilane, and 157 µl, (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.65 ppm indicative of the signal assigned to proton on silicon-adjoining carbon in the desired product was observed, from which a yield was computed. The results are shown in Table 3.

TABLE 3

| | NHC ligand | Hydrosilane | Conversion (%) | Yield (%) |
|---|---|---|---|---|
| Example 24 | IMes | 1,1,1,3,5,5,5-heptamethyl-trisiloxane | >99 | 69 |
| Example 25 | IPr | 1,1,1,3,5,5,5-heptamethyl-trisiloxane | >99 | 34 |
| Example 26 | IMes | ethyldimethylsilane | >99 | 78 |
| Example 27 | IMes | trimethoxysilane | >99 | 40 |

(6) Hydrosilylation Reaction of 2-norbornene with Various Hydrosilanes Using Cobalt Pivalate and NHC Ligand

[Chemical Formula 10]

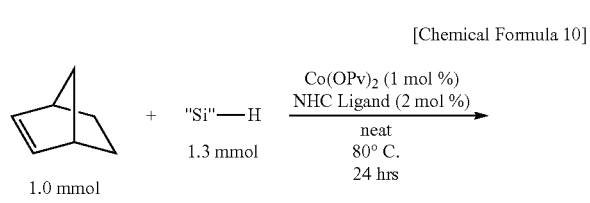

Example 28

Hydrosilylation Reaction of 2-norbornene with 1,1,3,3,3-pentamethyldisiloxane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 254 µL (1.3 mmol) of 1,1,3,3,3-pentamethyldisiloxane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.49 ppm indicative of the signal assigned to proton on silicon-adjoining carbon in the desired product was observed, from which a yield was computed. The results are shown in Table 4.

Example 29

Hydrosilylation Reaction of 2-norbornene with Dimethylphenylsilane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 202 µL (1.3 mmol) of dimethylphenylsilane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.81 ppm indicative of the signal assigned to proton on silicon-adjoining carbon in the desired product was observed, from which a yield was computed. The results are shown in Table 4.

Example 30

Hydrosilylation Reaction of Example 29 Using IPr as Ligand

Reaction was carried out according to the same procedure as in Example 29 aside from using 8 mg (0.02 mmol) of IPr instead of IMes as a ligand. As a result, it was confirmed that the signal assigned to the reactant diminished. Instead, a multiplet at 0.81 ppm indicative of the signal assigned to proton on silicon-adjoining carbon in the desired product was observed, from which a yield was computed. The results are shown in Table 4.

Example 31

Hydrosilylation Reaction of 2-norbornene with Trimethoxysilane Using Cobalt Pivalate and IMes A screw-top vial was charged with 3 mg (0.01 mmol) of cobalt pivalate in Synthesis Example 3 as a catalyst, 6 mg (0.02 mmol) of IMes as a NHC ligand, 165 µL (1.3 mmol) of trimethoxysilane as a hydrosilane, and 94 mg (1.0 mmol) of 2-norbornene. The contents were stirred at 80° C. for 24 hours. After cooling, analysis was made by $^1$H-NMR spectroscopy to determine the structure and yield of the product. As a result, it was confirmed that the signal assigned to the reactant disappeared completely. Instead, a multiplet at 0.76 ppm indicative of the signal assigned to proton on silicon-adjoining carbon in the desired product was observed, from which a yield was computed. The results are shown in Table 4.

Example 32

Hydrosilylation Reaction of Example 31 Using IPr as Ligand

Reaction was carried out according to the same procedure as in Example 31 aside from using 8 mg (0.02 mmol) of IPr instead of IMes as a ligand. As a result, it was confirmed that the signal assigned to the reactant diminished. Instead, a multiplet at 0.76 ppm indicative of the signal assigned to proton on silicon-adjoining carbon in the desired product was observed, from which a yield was computed. The results are shown in Table 4.

TABLE 4

|  | NHC ligand | Hydrosilane | Conversion (%) | Yield (%) |
| --- | --- | --- | --- | --- |
| Example 28 | IMes | 1,1,3,3,3-pentamethyldisiloxane | >99 | 83 |
| Example 29 | IMes | dimethylphenylsilane | >99 | 77 |
| Example 30 | IPr | dimethylphenylsilane | >99 | 73 |
| Example 31 | IMes | trimethoxysilane | >99 | 54 |
| Example 32 | IPr | trimethoxysilane | >99 | 68 |

Synthesis Example 7

Synthesis of Cobalt Carboxylate C

A 1 L flask equipped with a reflux tube was charged with 184.0 g (1.0 mol) of 10-undecylenic acid and 150.0 g of toluene and heated at 80° C. Then 100.6 g (0.625 mol) of hexamethyldisilazane was added dropwise to the solution, which was heated at 80° C. for a further 3 hours. The volatile component was removed by heating at 100° C. in vacuum, obtaining $CH_2=CH(CH_2)_8COOSiMe_3$ (Silylated product A) (254.4 g, yield 99.4%).

A 1 L flask equipped with a reflux tube was charged with 254.4 g (0.99 mol) of Silylated product A and 100.0 g of toluene and heated at 90° C. To the solution, 0.5 g of a toluene solution of 0.5 wt % chloroplatinic acid was added, and 264.7 g (1.19 mol) of 1,1,1,3,5,5,5-heptamethyltrisiloxane was added dropwise. At the end of dropwise addition, the solution was heated at 100° C. for a further 2 hours. The volatile component was removed by heating at 120° C. in vacuum, obtaining $(Me_3SiO)_2MeSi(CH_2)_{10}COOSiMe_3$ (Adduct A) (451.2 g, yield 95.0%).

A 1 L flask was charged with 239.0 g (0.5 mol) of Adduct A and 140.0 g of methanol, which were stirred at room temperature for 14 hours. Distillation gave the desired product: $(Me_3SiO)_2MeSi(CH_2)_{10}COOH$ (boiling point 175.0-176.0° C./0.3 kPa, amount 162.4 g, yield 80.0%). It had a purity of 99.5% as measured by gas chromatography.

Figure 5:
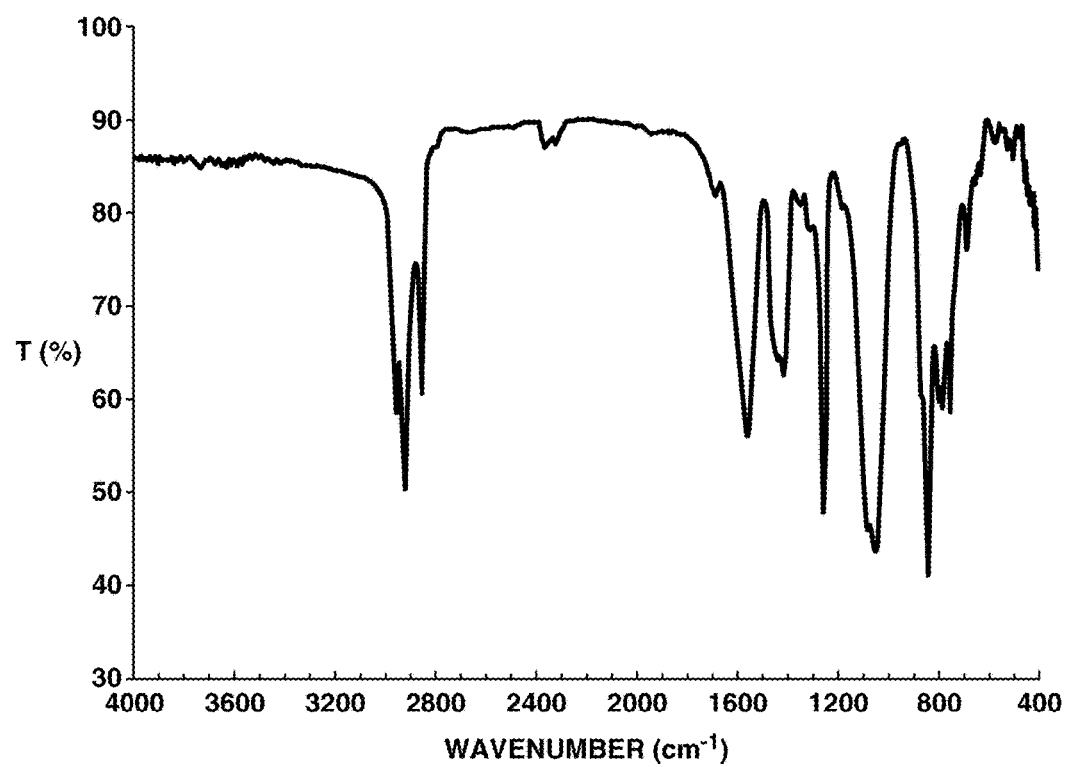
FIG. 5 is a diagram of the FT-IR spectrum of cobalt carboxylate C obtained in Synthesis Example 7.

In a 20 mL recovery flask, 0.43 g (2.41 mmol) of cobalt acetate and 2.0 g (4.92 mmol) of $(Me_3SiO)_2MeSi(CH_2)_{10}COOH$ were fed and stirred at 180° C. for 1 hour. Thereafter, the reaction mixture was vacuum dried at the temperature for 1 hour, obtaining cobalt carboxylate C. The FT-IR spectrum of cobalt carboxylate C is shown in FIG. 5.

FT-IR (KBr) ν: 2958, 2924, 2583, 1555, 1413, 1257, 1078, 1049, 842, 799, 783, 754, 687

(7) Hydrosilylation Reaction of 1-octene with Various Silanes Using Cobalt Carboxylate C and IMes

[Chemical Formula 11]

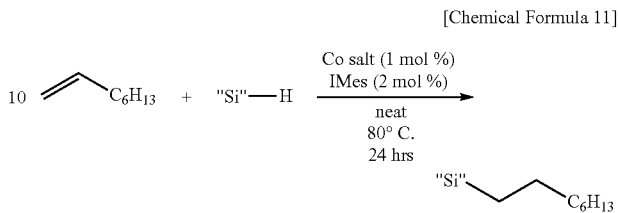

Example 33

Hydrosilylation Reaction of 1-octene with 1,1,3,3,3-pentamethyldisiloxane Using Cobalt Carboxylate C and IMes A screw-top vial was charged with 9 mg (0.01 mmol) of cobalt carboxylate C in Synthesis Example 7 as a catalyst, 6 mg (0.02 mmol) of IMes as a NHC ligand, 254 μL (1.3 mmol) of 1,1,3,3,3-pentamethyldisiloxane as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.50 ppm indicative of the signal assigned to proton on silicon-adjoining carbon in the desired product was observed, from which a yield was computed. The results are shown in Table 5.

Example 34

Hydrosilylation Reaction of 1-octene with Dual End Hydrodimethylsiloxy-blocked Polydimethylsiloxane Using Cobalt Carboxylate C and IMes A screw-top vial was charged with 9 mg (0.01 mmol) of cobalt carboxylate C in Synthesis Example 7 as a catalyst, 6 mg (0.02 mmol) of IMes as a NHC ligand, 1.07 g (0.50 mmol) of dual end hydrodimethylsiloxy-blocked polydimethylsiloxane (DOP 27) as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.50 ppm indicative of the signal assigned to proton on silicon-adjoining carbon in the desired product was observed, from which a yield was computed. The results are shown in Table 5.

TABLE 5

|  | Cobalt salt | Hydrosilane | Conversion (%) | Yield (%) |
| --- | --- | --- | --- | --- |
| Example 33 | cobalt carboxylate C | 1,1,3,3,3-pentamethyl-disiloxane | >99 | 63 |

TABLE 5-continued

| | Cobalt salt | Hydrosilane | Conversion (%) | Yield (%) |
|---|---|---|---|---|
| Example 34 | cobalt carboxylate C | dual end hydrodimethylsiloxy-blocked polydimethylsiloxane (DOP 27) | >99 | 67 |

(8) Hydrosilylation Reaction of 1-octene with Dual End Hydrosilane-Terminated Polydimethylsiloxane Using Cobalt Pivalate and IMes

[Chemical Formula 12]

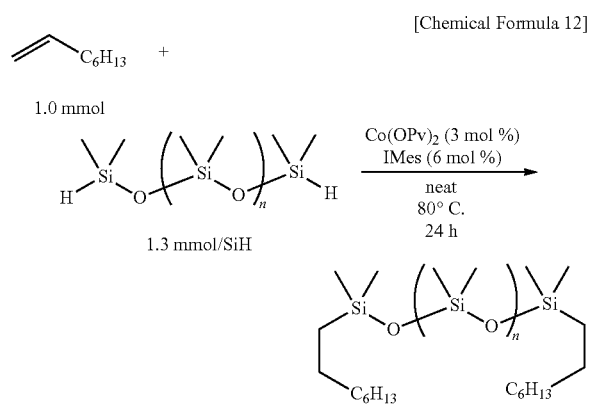

Example 35

A screw-top vial was charged with 8 mg (0.03 mmol) of cobalt pivalate in Synthesis Example 3 as a catalyst, 18 mg (0.06 mmol) of IMes as a NHC ligand, 1.39 g (0.65 mmol) of dual end hydrosilane-terminated polydimethylsiloxane (DOP 27) as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.65 ppm indicative of the signal assigned to proton on silicon-adjoining carbon in the desired product was observed, from which a yield was computed. The results are shown in Table 6.

TABLE 6

| | Metal salt | Conversion (%) | Yield (%) |
|---|---|---|---|
| Example 35 | cobalt pivalate | >99 | 85 |

Synthesis Example 8

Synthesis of Cobalt Carboxylate D

A 500 mL flask equipped with a reflux tube was charged with 100.0 g (1.16 mol) of 3-butenoic acid and 80.0 g of hexane and heated at 70° C. Then 117.0 g (0.73 mol) of hexamethyldisilazane was added dropwise to the solution, which was heated at 70° C. for a further 3 hours. The reaction solution was distilled, obtaining the desired compound $CH_2=CHCH_2COOSiMe_3$ (Silylated product B) (b.p. 60.0-62.0° C./5.3 kPa, amount 155.1 g, yield 84.6%). It had a purity of 94.4% as measured by gas chromatography.

A 500 mL flask equipped with a reflux tube was charged with 155.1 g (0.98 mol) of Silylated product B and 150.0 g of toluene and heated at 90° C. To the solution, 0.5 g of a toluene solution of 0.5 wt % chloroplatinic acid was added, and 239.8 g (1.08 mol) of 1,1,1,3,5,5,5-heptamethyltrisiloxane was added dropwise. At the end of dropwise addition, the solution was heated at 100° C. for a further 2 hours. The reaction solution was distilled, obtaining the desired product: $(Me_3SiO)_2MeSi(CH_2)_3COOSiMe_3$ (Adduct B) (b.p. 97.0-98.5° C./0.3 kPa, amount 253.8 g, yield 68.1%). It had a purity of 98.7% as measured by gas chromatography.

Next, a 500 mL flask was charged with 207.5 g (0.55 mol) of Adduct B and 100.0 g of methanol, which were stirred at room temperature for 14 hours. Distillation gave the desired product: $(Me_3SiO)_2MeSi(CH_2)_3COOH$ (b.p. 119.5-121.0° C./0.3 kPa, amount 109.5 g, yield 64.6%). It had a purity of 98.9% as measured by gas chromatography.

Figure 6:
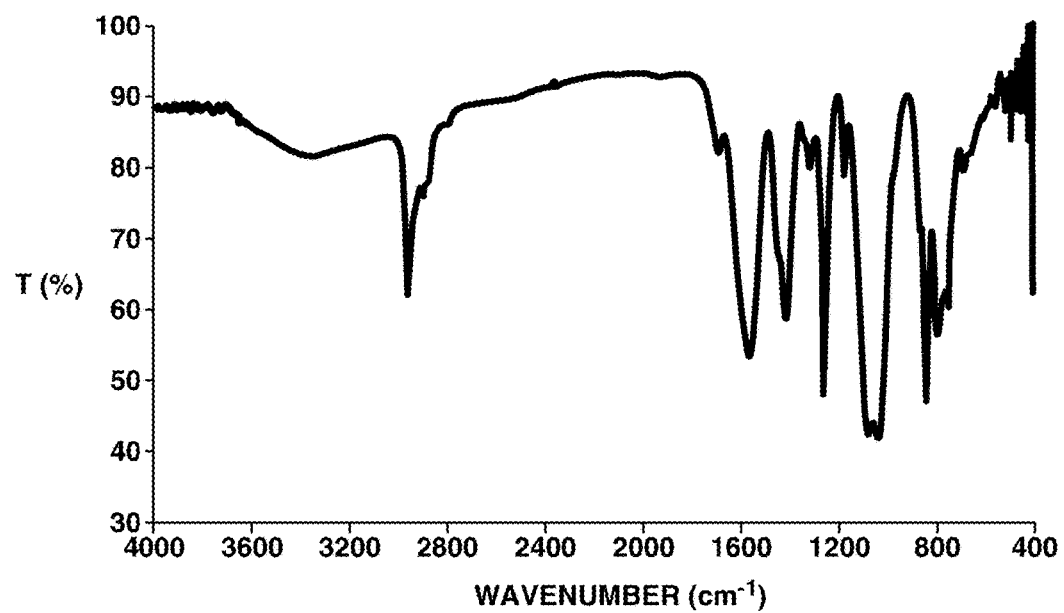
FIG. 6 is a diagram of the FT-IR spectrum of cobalt carboxylate D obtained in Synthesis Example 8.

In a 20 mL recovery flask, 0.20 g (1.13 mmol) of cobalt acetate and 0.70 g (2.28 mmol) of $(Me_3SiO)_2MeSi(CH_2)_3COOH$ were fed and stirred at 160° C. for 1 hour. Thereafter, the reaction mixture was vacuum dried at the temperature for 1 hour, obtaining cobalt carboxylate D. The FT-IR spectrum of cobalt carboxylate D is shown in FIG. 6.

FT-IR (KBr) v: 2958, 2901, 2880, 1686, 1561, 1413, 1259, 1176, 1078, 1041, 842, 797, 755

Synthesis Example 9

Synthesis of Cobalt Carboxylate E

A 1 L flask equipped with a reflux tube was charged with 184.0 g (1.0 mol) of 10-undecylenic acid and 150.0 g of toluene and heated at 80° C. Then 100.6 g (0.625 mol) of hexamethyldisilazane was added dropwise to the solution, which was heated at 80° C. for a further 3 hours. The volatile component was removed by heating at 100° C. in vacuum, obtaining $CH_2=CH(CH_2)_8COOSiMe_3$ (identical with Silylated product A in Synthesis Example 7) (amount 254.3 g, yield 99.3%).

A 1 L flask equipped with a reflux tube was charged with 51.2 g (0.20 mol) of Silylated product A and heated at 90° C. To the flask, 0.2 g of a toluene solution of 0.5 wt % chloroplatinic acid was added, and 94.5 g (0.23 mol) of $nBu(Me_2)SiO(Me_2SiO)_3Si(Me_2)H$ was added dropwise. At the end of dropwise addition, the solution was heated at 100° C. for a further 2 hours. The unreacted fractions were removed by heating at 200° C. in vacuum, obtaining the desired product: $nBu(Me_2)SiO(Me_2SiO)_3Si(Me_2)(CH_2)_{10}COOSiMe_3$ (Adduct C) (amount 127.0 g, yield 95.0%).

A 500 mL flask was charged with 127.0 g (0.19 mol) of Adduct C and 100.0 g of methanol, which were stirred at room temperature for 14 hours. The volatile component was removed by heating at 100° C. in vacuum, obtaining the desired product: $nBu(Me_2)SiO(Me_2SiO)_3Si(Me_2)(CH_2)_{10}COOH$ (amount 111.0 g, yield 98.0%). It had a purity of 99.8% as measured by gas chromatography.

Figure 7:
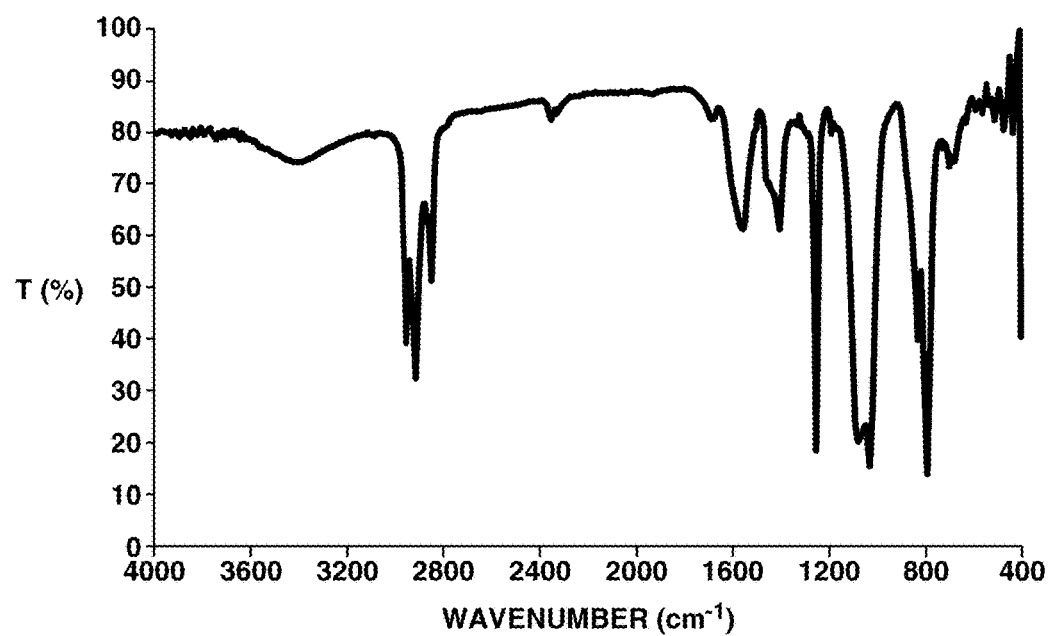
FIG. 7 is a diagram of the FT-IR spectrum of cobalt carboxylate E obtained in Synthesis Example 9.

In a 20 mL recovery flask, 0.20 g (1.13 mmol) of cobalt acetate and 1.35 g (2.26 mmol) of $nBu(Me_2SiO)_5(CH_2)_{10}COOH$ were fed and stirred at 160° C. for 1 hour. Thereafter, the reaction mixture was vacuum dried at the temperature for 1 hour, obtaining cobalt carboxylate E. The FT-IR spectrum of cobalt carboxylate E is shown in FIG. 7.

FT-IR (KBr) v: 2960, 2924, 2854, 1560, 1457, 1412, 1259, 1088, 1037, 840, 798

(9) Hydrosilylation Reaction of 1-octene with 1,1,3,3,3-pentamethyldisiloxane Using Cobalt Carboxylate D or Cobalt Carboxylate E and IMes

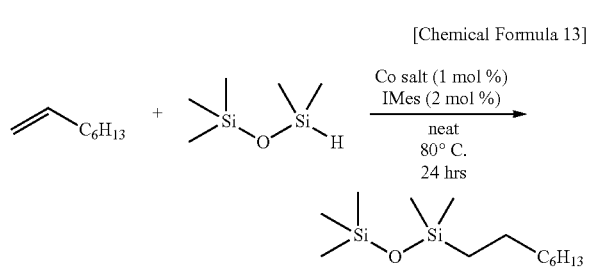

Example 36

Hydrosilylation Reaction of 1-octene with 1,1,3,3,3-pentamethyldisiloxane Using Cobalt Carboxylate D and IMes A screw-top vial was charged with 7 mg (0.01 mmol) of cobalt carboxylate D in Synthesis Example 7 as a catalyst, 6 mg (0.02 mmol) of IMes as a NHC ligand, 254 μL (1.3 mmol) of 1,1,3,3,3-pentamethyldisiloxane as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.50 ppm indicative of the signal assigned to proton on silicon-adjoining carbon in the desired product was observed, from which a yield was computed. The results are shown in Table 7.

Example 37

Hydrosilylation Reaction of 1-octene with 1,1,3,3,3-pentamethyldisiloxane Using Cobalt Carboxylate E and IMes A screw-top vial was charged with 13 mg (0.01 mmol) of cobalt carboxylate E in Synthesis Example 8 as a catalyst, 6 mg (0.02 mmol) of IMes as a NHC ligand, 254 μL (1.3 mmol) of 1,1,3,3,3-pentamethyldisiloxane as a hydrosilane, and 157 μL (1.0 mmol) of 1-octene. The contents were stirred at 80° C. for 24 hours. After cooling, analysis was made by $^1$H-NMR spectroscopy to determine the structure and yield of the product. As a result, it was confirmed that the signal assigned to the reactant disappeared. Instead, a multiplet near 0.50 ppm indicative of the signal assigned to proton on silicon-adjoining carbon in the desired product was observed, from which a yield was computed. The results are shown in Table 7.

TABLE 7

|  | Cobalt salt | Conversion (%) | Yield (%) |
|---|---|---|---|
| Example 36 | cobalt carboxylate D | >99 | 77 |
| Example 37 | cobalt carboxylate E | >99 | 82 |

(10) Hydrosilylation of 1-octene with 1,1,3,3,3-pentamethyldisiloxane Using Complex having Nickel-oxygen Bond and NHC Ligand

Example 38

Hydrosilylation Reaction of 1-octene with 1,1,3,3,3-pentamethyldisiloxane Using Nickel Acetate and IPr A screw-top vial was charged with 5 mg (0.03 mmol) of nickel acetate as a catalyst precursor, 23 mg (0.06 mmol) of IPr as a NHC ligand, 254 μL (1.3 mmol) of 1,1,3,3,3-pentamethyldisiloxane, and 157 μL (1.0 mmol) of 1-octene. The contents were stirred at 80° C. for 24 hours. After cooling, analysis was made by the internal standard method to find a substrate conversion of 32% and formation of 1,1,1,3,3-pentamethyl-3-octyldisiloxane in a yield of 27% and an isomerized compound of 1-octene, internal octene in a yield of 5%.

The invention claimed is:
1. A hydrosilylation reaction catalyst which is prepared from:
a metal salt compound having the formula (1):

$$M_a(L)_b(X)_c \qquad (1)$$

wherein (i) M is Fe, Co or Ni, a is 1, b is 2, and c is 0; (ii) M is Rh, a is 2, b is 4, and c is 0; or (iii) M is Ru, a is 2, b is 4, and c is 1,
X is a halogen atom,
L is a monovalent organic group of at least one type selected from the formulae (3) to (5), $$-O-R^1 \qquad (3)$$

$$-OCO-R^1 \qquad (4)$$

$$-OSO_2-R^1 \qquad (5)$$

wherein $R^1$ is each independently an optionally substituted, $C_1$-$C_{30}$ monovalent organic group which may be separated by at least one atom selected from oxygen, nitrogen, sulfur and phosphorus, or a monovalent organic group having the formula (6):

$$-(A)_p-R^2 \qquad (6)$$

wherein A is a $C_1$-$C_{30}$ divalent organic group which may be substituted with halogen,
p is an integer of 0 or 1, satisfying p =0 or 1 when L is a monovalent organic group having formula (3), and p =1 when L is a monovalent organic group having formula (4) or (5),
$R^2$ is a group having the formula (7):

$$-\{Si(R^3)_2-R^4\}_s-Si(R^3)_d\{[(OSi(R^3)_2)]_f-R^3\}_e \qquad (7)$$

wherein $R^3$ is each independently an optionally substituted, $C_1$-$C_{20}$ alkyl group, $C_1$-$C_{20}$ alkoxy group, $C_6$-$C_{20}$ aryl group or $C_7$-$C_{20}$ aralkyl group which may be separated by at least one atom selected from oxygen, nitrogen, sulfur and phosphorus, $R^4$ is a $C_1$-$C_{10}$ divalent hydrocarbon group, s is an integer of 0 or 1, d is an integer of 0 to 3, e is an integer of 0 to 3, satisfying d+e =3, and f is an integer of 1 to 300, and
a carbene compound having one or two adjoining nitrogen atoms, represented by the formula (2):

[Chemical Formula 1]

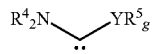
(2)

wherein Y is a carbon, nitrogen or oxygen atom, g is 3 when Y is carbon, g is 2 when Y is nitrogen, g is 1 when Y is oxygen, $R^4$ and $R^5$ are each independently a $C_1$-$C_{30}$ alkyl, aryl or aralkyl group which may be substituted with a halogen atom or alkoxy group, and any one of $R^4$ and any one of $R^5$ may bond together to form a divalent organic group so that the compound has a cyclic structure which may contain a nitrogen atom and/or unsaturated bond.

2. The hydrosilylation reaction catalyst of claim 1 wherein in formula (7), s is 0.

3. The hydrosilylation reaction catalyst of claim 1 which is prepared in a system where hydrosilylation reaction of a compound having an aliphatic unsaturated bond with a hydrosilane compound having a Si—H group or organohydropolysiloxane compound is carried out.

4. The hydrosilylation reaction catalyst of claim 1 wherein the carbene compound of formula (2) has the formula (8):

[Chemical Formula 2]

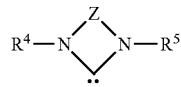
(8)

wherein Z is a $C_2$-$C_5$ divalent organic group which may contain a nitrogen atom and/or unsaturated bond, $R^4$ and $R^5$ are each independently a $C_1$-$C_{30}$ alkyl, aryl or aralkyl group which may be substituted with a halogen atom or alkoxy group.

5. The hydrosilylation reaction catalyst of claim 1 wherein L is a monovalent organic group having formula (4).

6. A method for preparing an addition compound comprising the step of carrying out hydrosilylation reaction of a compound having an aliphatic unsaturated bond with a hydrosilane compound having a Si—H group or organohydropolysiloxane compound in the presence of the hydrosilylation reaction catalyst of claim 1.

7. The method for preparing an addition compound of claim 6 wherein the compound having an aliphatic unsaturated bond is an organopolysiloxane having an alkenyl group.

* * * * *